US012023423B2

(12) United States Patent
Chase

(10) Patent No.: US 12,023,423 B2
(45) Date of Patent: Jul. 2, 2024

(54) AIRBORNE PATHOGEN EXTRACTION SYSTEM

(71) Applicant: Arnold Chase, West Hartford, CT (US)

(72) Inventor: Arnold Chase, West Hartford, CT (US)

( * ) Notice: Subject to any disclaimer, the term of this patent is extended or adjusted under 35 U.S.C. 154(b) by 0 days.

(21) Appl. No.: 17/976,252

(22) Filed: Oct. 28, 2022

(65) Prior Publication Data

US 2023/0058361 A1 Feb. 23, 2023

Related U.S. Application Data

(60) Division of application No. 17/087,285, filed on Nov. 2, 2020, now Pat. No. 11,484,620, which is a continuation-in-part of application No. 16/911,640, filed on Jun. 25, 2020, now Pat. No. 10,821,202.

(51) Int. Cl.
*A61L 9/20* (2006.01)
*A61G 13/10* (2006.01)
*B01D 46/00* (2022.01)
*B01D 46/42* (2006.01)

(52) U.S. Cl.
CPC .............. *A61L 9/20* (2013.01); *A61G 13/108* (2013.01); *B01D 46/00* (2013.01); *B01D 46/0002* (2013.01); *B01D 46/0028* (2013.01); *B01D 46/42* (2013.01); *A61L 2209/11* (2013.01)

(58) Field of Classification Search
CPC ... A61L 9/20; A61M 16/009; A61M 16/1065; B01D 46/00; B01D 46/0023; B01D 46/0028
See application file for complete search history.

(56) References Cited

FOREIGN PATENT DOCUMENTS

DE          3734762 A1 *  3/1989
JP          H0416252 A *  1/1992

* cited by examiner

*Primary Examiner* — Robert A Hopkins
(74) *Attorney, Agent, or Firm* — McCormick, Paulding & Huber PLLC

(57) ABSTRACT

An airborne pathogen extraction system that provides for continuous airborne pathogen particle extraction from a specifically targeted area in a room or a specifically targeted area proximate to a user. The pathogenic particles are filtered and/or disinfected before the air is returned proximate to the originating location, or are directed an area away from the user(s). The airborne pathogen extraction systems and methods lower the chances of contagion or infection from airborne pathogens, such as viruses.

8 Claims, 14 Drawing Sheets

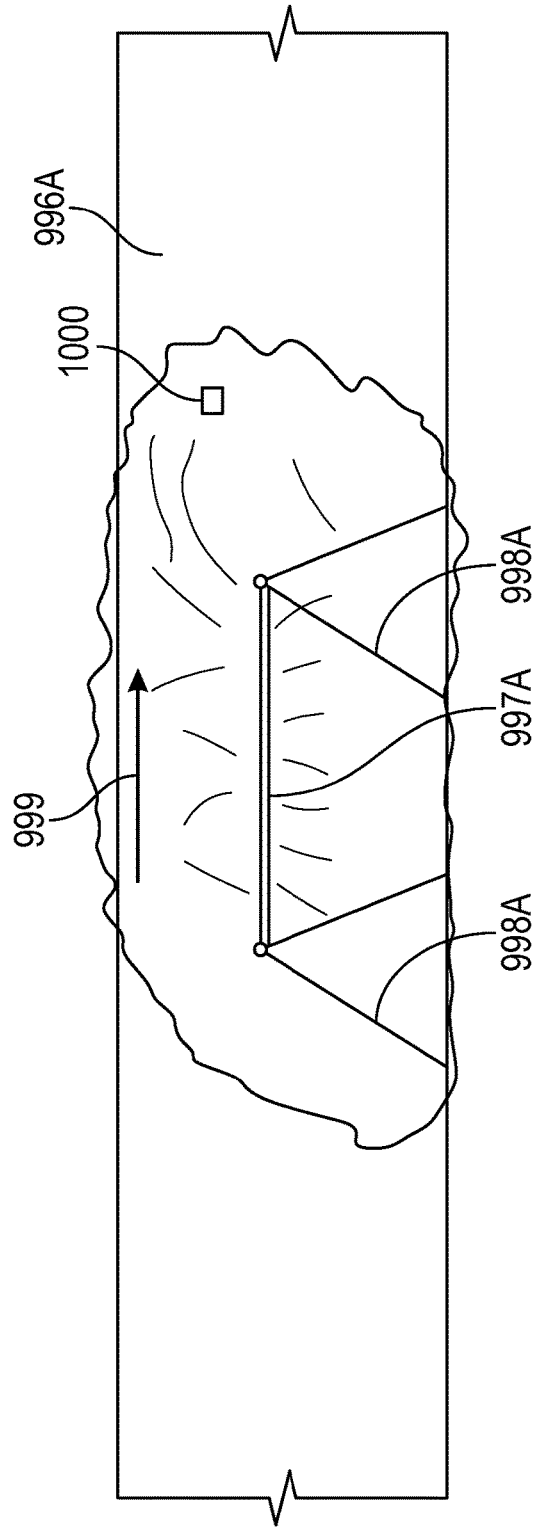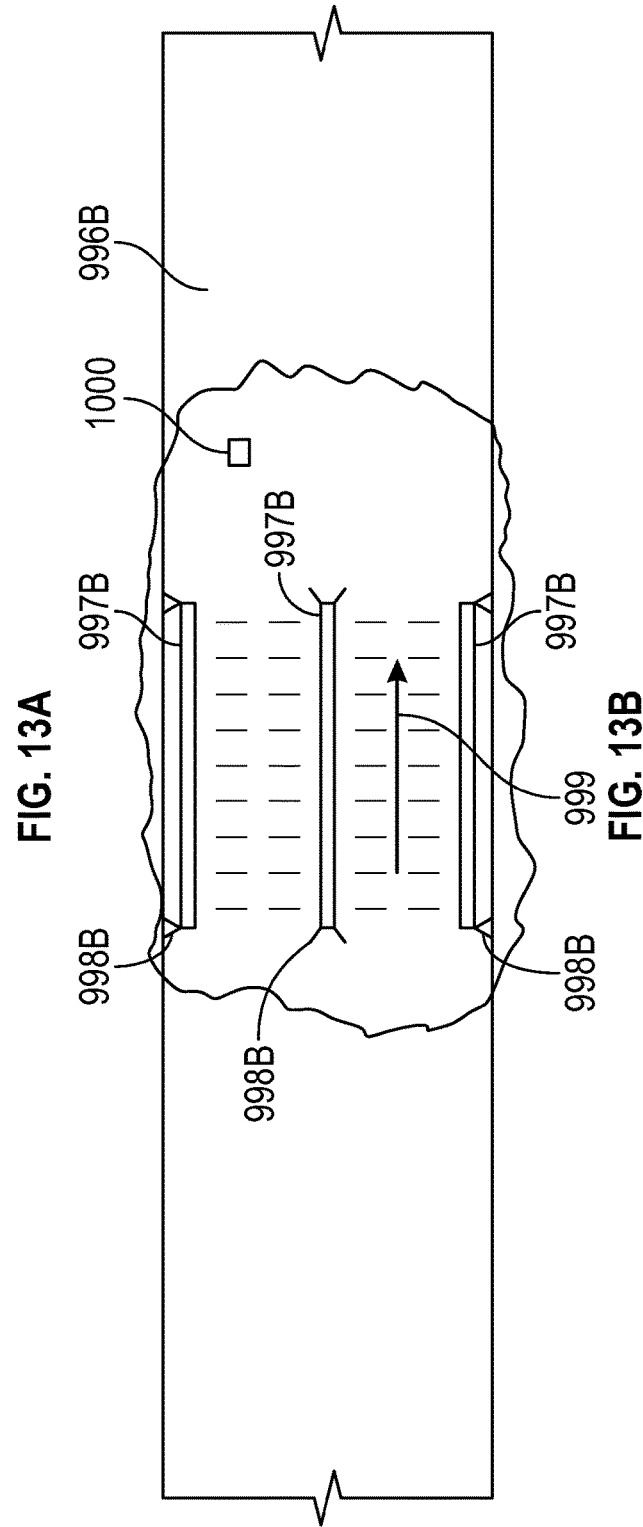

AIRBORNE PATHOGEN EXTRACTION SYSTEM

CROSS-REFERENCE TO RELATED APPLICATIONS

This application is a divisional of U.S. patent application Ser. No. 17/087,285, filed Nov. 2, 2020, which is a continuation-in-part of U.S. patent application Ser. No. 16/911,640, filed on Jun. 25, 2020, which is hereby incorporated by reference in its entirety.

TECHNICAL FIELD

The present disclosure relates to airborne pathogen extraction systems and, more particularly, airborne pathogen extraction system with a focus on extracting airborne pathogens proximate to one or more users.

BACKGROUND

With the increasing prevalence of highly contagious viruses and other pathogens, research has shown a direct relationship between the inhaled quantity of infectious aerosolized pathogen particles and the chance for infection by individuals in an area containing said particles. As a result of this reality, certain activities that encompass close proximity to the head area, such as dental procedures, hair styling, optical testing and other activities, which by their very nature require a close and prolonged proximity between the head area of two or more people, which create a potentially hazardous infection situation. The only mitigation solution known to effectively eliminate the chance of infection due to these activities that have such an inherent increased infection potential is to no longer undertake the activities except in emergency situations. While cancelling numerous such routine procedures may achieve the desired potential infection mitigation, the direct benefit provided by the cancelation of such activities is offset by the creation of numerous secondary health problems due to the cancelation of the activities.

SUMMARY

Studies have shown that infected individuals, even asymptomatic ones, are capable of quickly shedding enough viral particles to infect numerous other individuals within a room or area. More significantly, these studies have also shown that those individuals closest to an infected individual are presented with the largest number of exhaled airborne infectious agents, and, as a result, those individuals not only become infected most quickly, but their health outcomes were far more serious, thus demonstrating a negative outcome link to the level of pathogen exposure. These studies have also shown that even those individuals that are located some distance away from a particular infected individual and are practicing "social distancing" can become infected, and it has been discovered that those distanced individuals become infected due to their location being downstream from the infected individual who is further upstream from the room's HVAC return air path. Individuals upstream from the infected person's position do not become infected to the same degree.

As a result of these studies, we now know that an active airflow stream is capable of carrying away airborne pathogen particles from an infected individual(s). With conventional HVAC systems, there is a continual airflow in an area utilizing a supply air ductwork to a corresponding return air ductwork. Even when conventional air filters are used within the HVAC system, the extremely small size of the pathogen particles (e.g. viruses) are mostly able to slip through a system's air filters and get returned to the room.

Specialty locations, such as isolation rooms in hospitals, use negative air pressure techniques or sterilization equipment such as UV-C lamps located in the ductwork to remove airborne pathogens and/or other airborne contaminants. Because these systems attempt to treat all of the air flowing through a large area, they are both costly and inefficient as they take a "shotgun" approach to air filtration and disinfection.

In contrast, if just a specific area of concern, such as, for example, the immediate vicinity between a dentist and a patient is treated, the efficiency at extracting virus or other pathogen particles from just that specific area becomes quite high. In accordance with principles of the present disclosure, an Airborne Pathogen Extraction System (APES) is provided that reduces the chances for a concentration of virus particles or other pathogens in a specific area to escalate to a level that presents a likely infection vector. Unlike traditional methods for treating the air in an entire area or room, the APES unit of the present disclosure is capable of almost instantly extracting airborne pathogens before they travel away from an individual and can be inhaled by a non-infected individual.

Figure 1A:
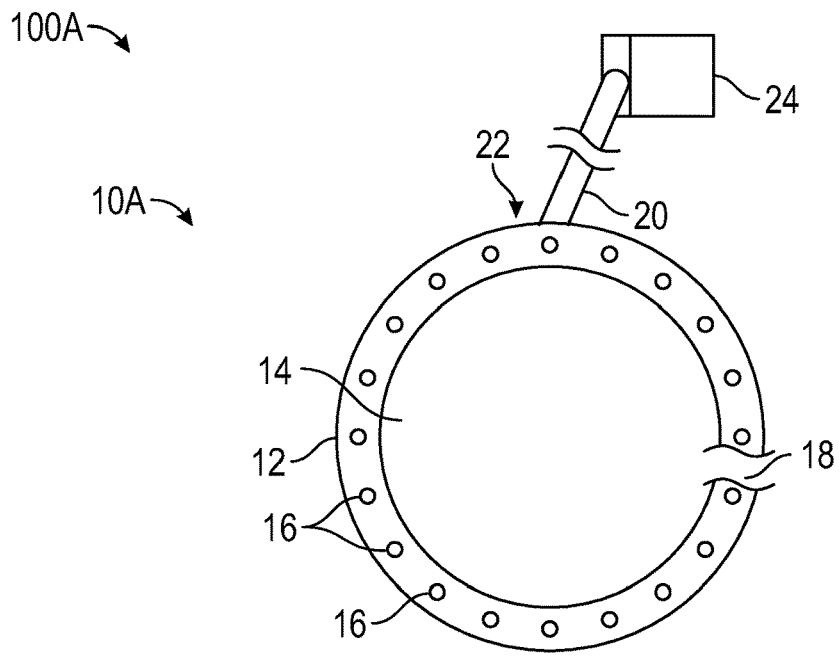
FIG. 1A shows a top view of an airborne pathogen extraction system having an extraction nozzle ring with an extraction air hose connector located at the rear of the extraction nozzle and an air disinfection unit in accordance with the present disclosure.
Figure 1B:
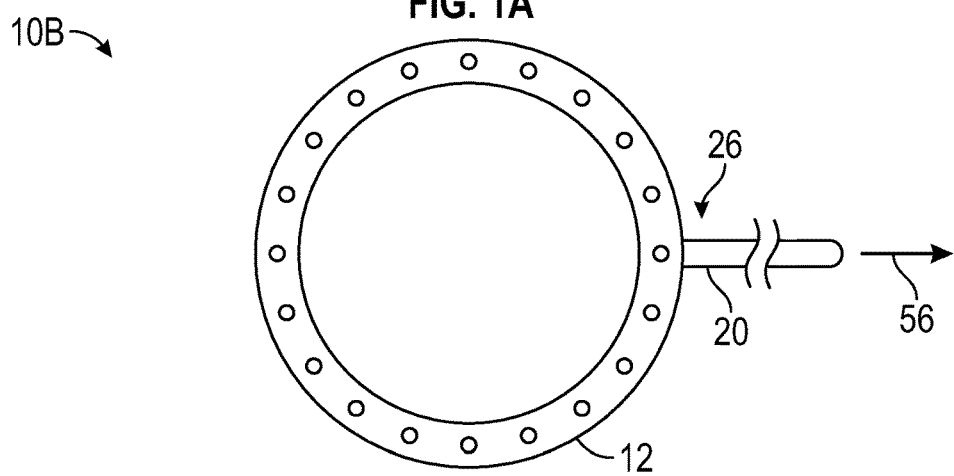
FIG. 1B shows a top view of an extraction nozzle ring with an extraction air hose connector located at a side of the extraction nozzle in accordance with the present disclosure.
Figure 1C:
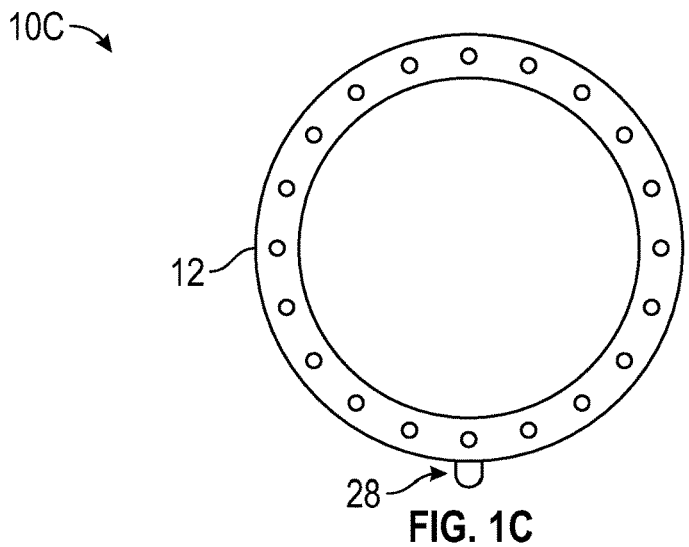
FIG. 1C shows a top view of an extraction nozzle ring with an extraction air hose connector located at the front of the extraction nozzle in accordance with the present disclosure.
Figure 1D:
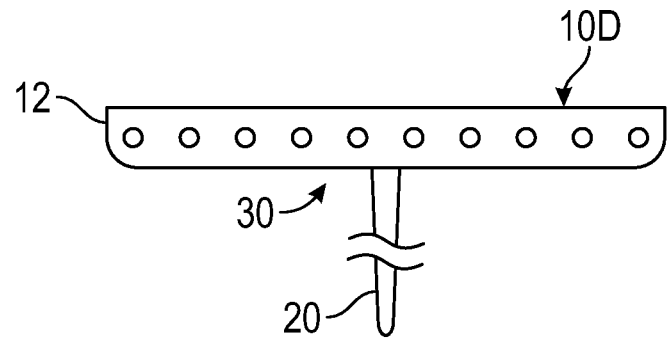
FIG. 1D shows a side view of an extraction nozzle ring with an air hose located at the bottom of the extraction nozzle in accordance with the present disclosure.
Figure 1E:
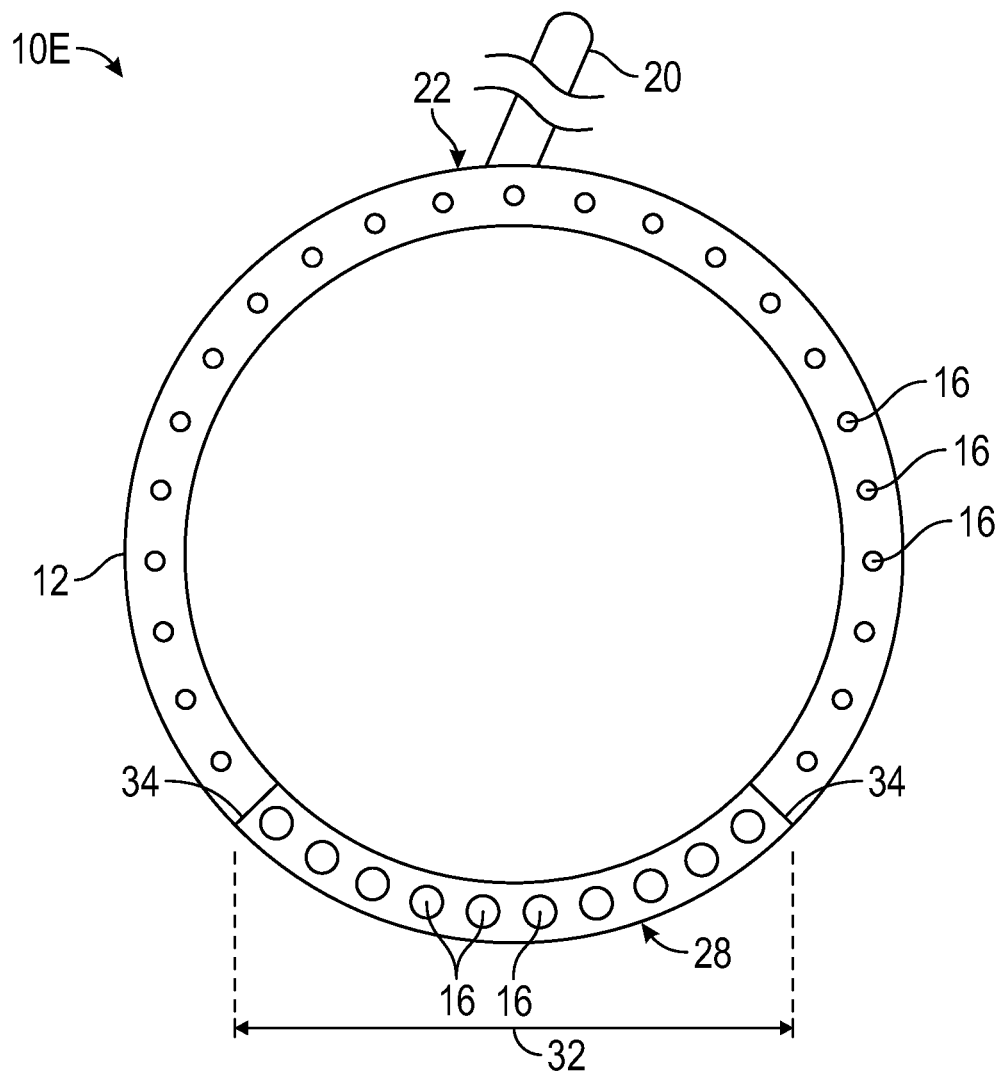
FIG. 1E shows a top view of an extraction nozzle ring in accordance with the present disclosure.
Figure 2:
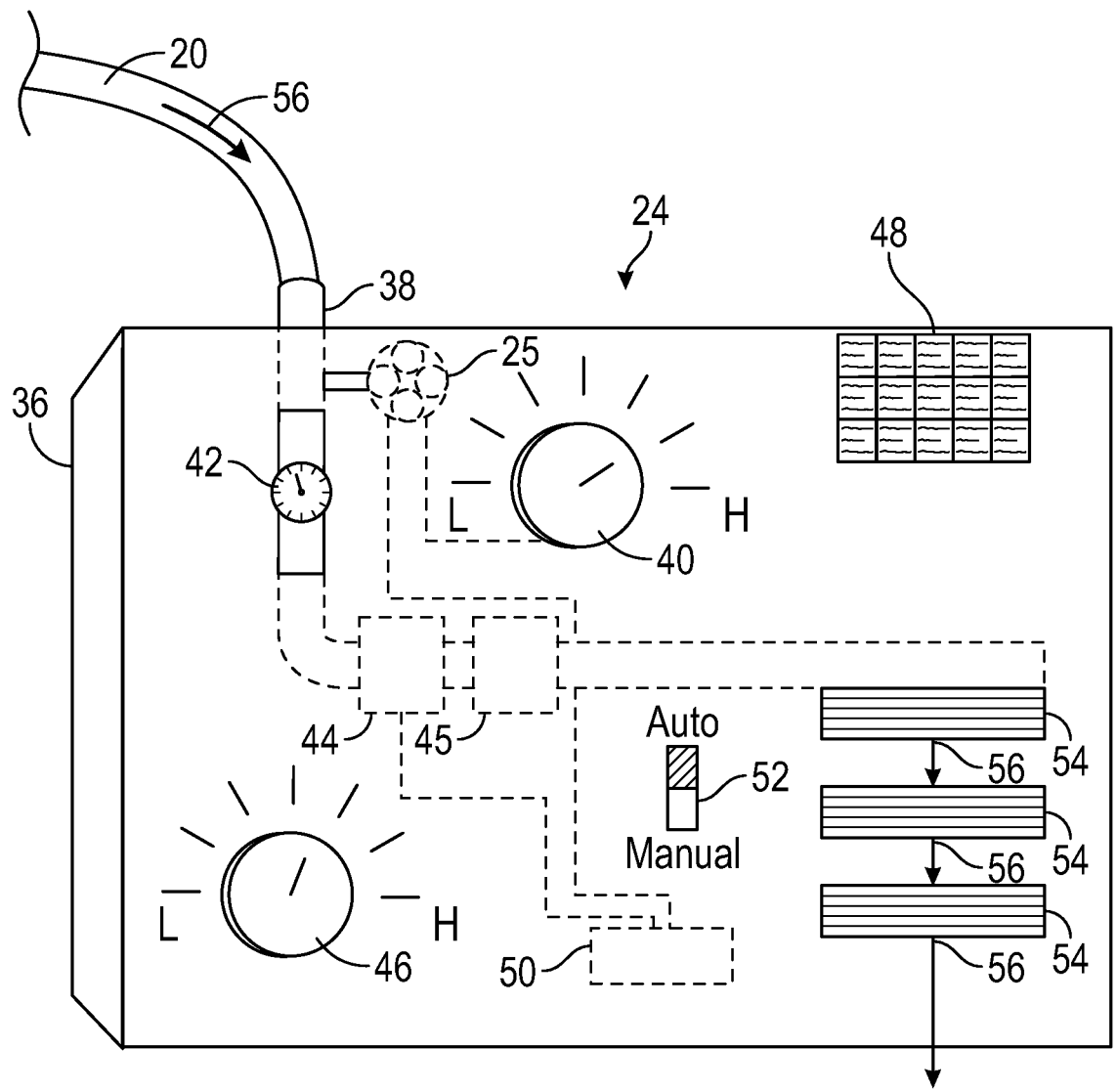
FIG. 2 shows a perspective view of the air disinfection unit of FIG. 1A in accordance with the present disclosure.

FIG. 13B shows an axial cutaway section of an air duct in accordance with the present disclosure;

FIG. 13C shows a radial cutaway section of the air duct of FIG. 13B in accordance with the present disclosure; and FIG. 13D shows a radial cutaway section of an air duct in accordance with the present disclosure.

DETAILED DESCRIPTION

Before the various embodiments are described in further detail, it is to be understood that the invention is not limited to the particular embodiments described. It is also to be understood that the terminology used is for the purpose of describing particular embodiments only, and is not intended to limit the scope of the claims of the present application.

In the drawings, like reference numerals refer to like features of the airborne pathogen extraction systems of the present application. Accordingly, although certain descriptions may refer only to certain figures and reference numerals, it should be understood that such descriptions might be equally applicable to like reference numerals in other figures. Additionally, although various features have been shown in different figures for simplicity, it should be readily apparent to one of skill in the art that the various features may be combined without departing from the scope of the present disclosure.

Referring to FIG. 1A, an Airborne Pathogen Extraction System (APES) 100A is shown in accordance with the present disclosure. The Airborne Pathogen Extraction System 100A includes an extraction nozzle ring 10A having a body 12 that is ring-shaped and defines a central opening 14. The central opening 14 is large enough to fit a neck and/or head of a user therein. The body 12 includes a plurality of air extraction openings 16 that each fluidly connect the environment exterior of the body 12 with an inner volume 18 defined by the body 12. The air extraction openings 16 are spaced about the circumference of the body 12. The body 12 is connected to a flexible air hose 20 at the rear 22 of the body 12. The air hose 20 is fluidly connected to an air disinfection unit 24 of the Airborne Pathogen Extraction System 100A, the structure and function of which is discussed in greater detail later herein.

In some embodiments, the connection of the air hose 20 to the extraction nozzle ring 10A may be at different radial (or horizontal) attachment points of the body 12. For example, referring to FIGS. 1B and 1C, which show extraction nozzle rings 10B and 10C, respectively, the air hose 20 may be connected at the side 26 of the body 12 (FIG. 1B) or at the front 28 of the body 12 (FIG. 1C). In some embodiments, the connection of the air hose 20 may be arranged axially (or vertically) from the body 12. For example, referring to FIG. 1D, which shows an extraction nozzle ring 10D, the air hose 20 may be connected to the bottom 30 of the body 12. The connection of the air hose 20 may be at any angle between a radial connection to the body 12 (i.e. FIGS. 1A-1C) and an axial connection to the body 12 (i.e. FIG. 1D). For example, the connection of the air hose 20 to the body 12 may be at a 45° angle from a plane aligned with the central opening 14. However, any angle of connection is within the scope of the present disclosure, such as, for example and without limitation, 15°, 30°, 60° or 75°.

The size, spacing, number and locations of the air extraction openings 16 may vary between embodiments. For example, referring to FIG. 1E, which shows an extraction nozzle ring 10E, the extraction nozzle ring 10E may include an area 32 having larger sized air extraction openings 16 and/or higher density of air extraction openings 16 (i.e. less distance or less average distance between adjacent air extraction openings 16 or having a greater number air extraction openings 16 per unit surface area of the extraction nozzle) than another area of the extraction nozzle ring 10E. In some embodiments, the air extraction openings 16 are only located in the area 32 and there are no air extraction openings 16 located elsewhere on the body 12. The area 32 may be a small portion of the extraction nozzle ring 10E than the remaining portion of the extraction nozzle ring 10E. For example and without limitation, the area 32 may constitute 30° or less, 60° or less, 90° or less, 120° or less, 150° or less of the angular extent of the circumference of the extraction nozzle ring 10E. In the extraction nozzle ring 10E, the area 32 is located at the front of the body 12 while the air hose 20 connection is at the rear of the body 12. The shape, size, location and number of the air extraction openings 16 is configured to shape, influence, and/or optimize the operation of the extraction nozzle ring 10 upon the air and possible pathogens in the vicinity of the extraction nozzle ring 10.

In some embodiments, one or more areas or sections of extraction nozzle ring 10 may be temporarily removable at connection points. For example, the area 32 of the extraction nozzle ring 10E of FIG. 1E is configured to be removed and reattached at the connection points 34. The areas or sections may be connected and/or disconnected through slip-fit or other known connection methods. The area 32 being removable and configured to reattach allows for insertion of user's neck within the central opening 14 if the central opening 14 is too small to fit the user's head. Removal also allows for cleaning or other maintenance of the extraction nozzle ring 10, or for replacement with a new portion.

The air disinfection unit 24 may vary in size and airflow capacity depending on the number of extraction nozzles 10 that are operatively connected to it. While typically the air disinfection unit 24 is designed for localized use with a single extraction nozzle ring 10, the air disinfection unit 24 may be scaled up to a larger capacity unit that may be designed to simultaneously accommodate multiple extraction nozzles 10 of varying design and capacity as well. The air disinfection unit 24 may be configured to operate from mains power and/or the air disinfection unit 24 may be configured to operate on internal rechargeable or non-rechargeable batteries as well.

Referring to FIG. 2, the air disinfection unit 24 of FIG. 1A is shown in greater detail. The air disinfection unit 24 includes a body 36 with an air input connector 38 that is fluidly connected to the air hose 20 of FIG. 1A. The air disinfection unit 24 includes an airflow generating means 25 configured to generate negative air pressure within the air hose 20 such that air in the environment exterior of the extraction nozzle ring 10A (FIG. 1A) flows through the air extraction openings 16, into the inner volume 18, into the air hose 20 and then in to the air disinfection unit 24. The phrase "negative air pressure" in the context of the present disclosure means an air pressure that is less than the air pressure of ambient air exterior to the extraction nozzle ring 10A. The negative air pressure may be generated by the air disinfection unit 24 through any one or more known structures and methods, including but not limited to one or more fans, one or more vacuum pumps, etc. The airflow rate is configured to be adjusted by a control element 40. The current airflow rate may be monitored at an input and/or output airflow meter 42. While the air disinfection unit 24 is shown with a single air input connector 38, the air disinfection unit 24 may be configured with any number of air input connectors 38 for connection with a plurality of air hoses 20 and extraction nozzles 10, or there may be a single air input connector 38 that utilizes an external manifold for connecting a plurality of air hoses 20 fluidly to the air disinfection unit 24.

The air disinfection unit 24 includes a light source 44 within the body 36 that is configured to generate a disinfecting light emission that acts on the air induced to flow into the air disinfection unit 24 from the extraction nozzle ring 10A. Either before or after the light source 44, the air may flow into an optional mechanical filter (or physical filter) 45 that mechanically filters the air via passive electrostatic media filtration, via actively electrostatic media filtration, or via other types of HEPA filtration. The intensity and/or emission frequency of the disinfecting light emission may be controlled by a control element 46, or there may be separate control elements 46 for light intensity and light emission frequency, respectively. For a manual operating mode, a chart 48 is attached to the air disinfection unit 24 to aid in matching the airflow speed setting with the required or desired disinfecting light intensity setting to optimize the effectiveness against a particular infectious vector. The input and/or output airflow meter 42 may provide an indication of the airflow rate at any selected setting to aid in airflow/intensity setting matching. Alternatively or additionally, the air disinfection unit 24 may be equipped with an automatic airflow speed/light intensity matching system configured to be executed by a controller 50 in an automatic operating mode. In the automatic mode, a selected fan speed (or induced air flow speed) through the control element 40 causes the controller 50 to instruct the light source 44 to operate at a predetermined light intensity and/or light emission frequency for the selected fan speed (or induced air flow speed). The predetermined light intensity and/or light emission frequency may increase with increasing fan speed (or induced air flow speed). In some embodiments, the operating light intensity and/or light emission frequency may be adjusted from the predetermined light intensity and light emission frequency, such that the automatic mode assists the user in providing an appropriate light source 44 intensity and/or emission frequency but still provides the user the ability to provide differing light source 44 control in order to address particular pathogen conditions. The air disinfection unit 24 may be provided with a mode selector switch 52 that is configured to switch the air disinfection unit 24 between the manual operating mode and the automatic operating mode. The air disinfection unit 24 includes one or more output vents with one or more louvers 54, which are angled to direct output airflow 56 downwards and outside the body 36 of the air disinfection unit 24 after the airflow has passed through the air disinfection unit 24 and been exposed to the light emissions from the light source 44. In other words, the output airflow 56 is directed towards the ground and away from the location of users after treatment and/or filtering. The air disinfection unit 24 may operate on internal batteries (rechargeable or disposable) and/or be configured to operate on an electric power connection to mains as discussed above.

In operation, the air disinfection unit 24 draws air in through the input connector 38 to generate a continuous negative air pressure in the air hose 20 that causes air exterior of the extraction nozzle ring(s) 10 to flow through the air extraction openings 16, into the inner volume 18, into the air hose 20, and in to the air disinfection unit 24. The airflow causes continuous extraction of airborne pathogens from the air in an area in the immediate vicinity (or proximate) to the extraction nozzle ring 10, which may be worn or utilized by a user whom may be shedding infectious pathogens. After the air has been directed to the air disinfection unit 24, the air may be filtered and/or treated, and then the air is returned to the room at a lower physical height than from where the air/pathogens were extracted from through the one or more output vents with one or more louvers 54. In some embodiments, the air disinfection unit 24 may direct the air to a location remote from the user (or other individuals) without filtering or treating the air at the air disinfection unit 24. In these embodiments, instead of vents with louvers 54, the output of the air disinfection unit 24 may be connected to an air ventilation distribution system to direct the air to the remote location. Even when the air disinfection unit 24 does not filter or treat the air before directing the air to a remote location, the air disinfection unit 24 may still be considered an air "disinfection" unit because the air proximate to the user or other individuals wearing or utilizing the extraction nozzle 10 is still being extracted from the vicinity of the user or other individuals, with potential pathogens being expelled by the user being drawn into the extraction nozzle 10. In some embodiments, the air flow generating means 25 is configured to extract pathogens within a distance of 6 inches, 12 inches, 18 inches or 24 inches from the extraction nozzle 10. However, other ranges of extraction are within scope of the present application and are dependent upon a number of factors, including but not limited to strength of the flow generating means 25 of the air disinfection unit 24, diameter and length of the air hose 20, size and number of the air extraction openings 16, and whether there are any obstructions of the air extraction openings 16 (e.g. due to clothing, dust, dirt, water, etc.). In some embodiments, the extraction nozzle 10 has a maximum extraction rating of 18 inches. The extraction rating represents an effective distance rating for effectively extracting pathogens from the extraction nozzle.

Figure 3:
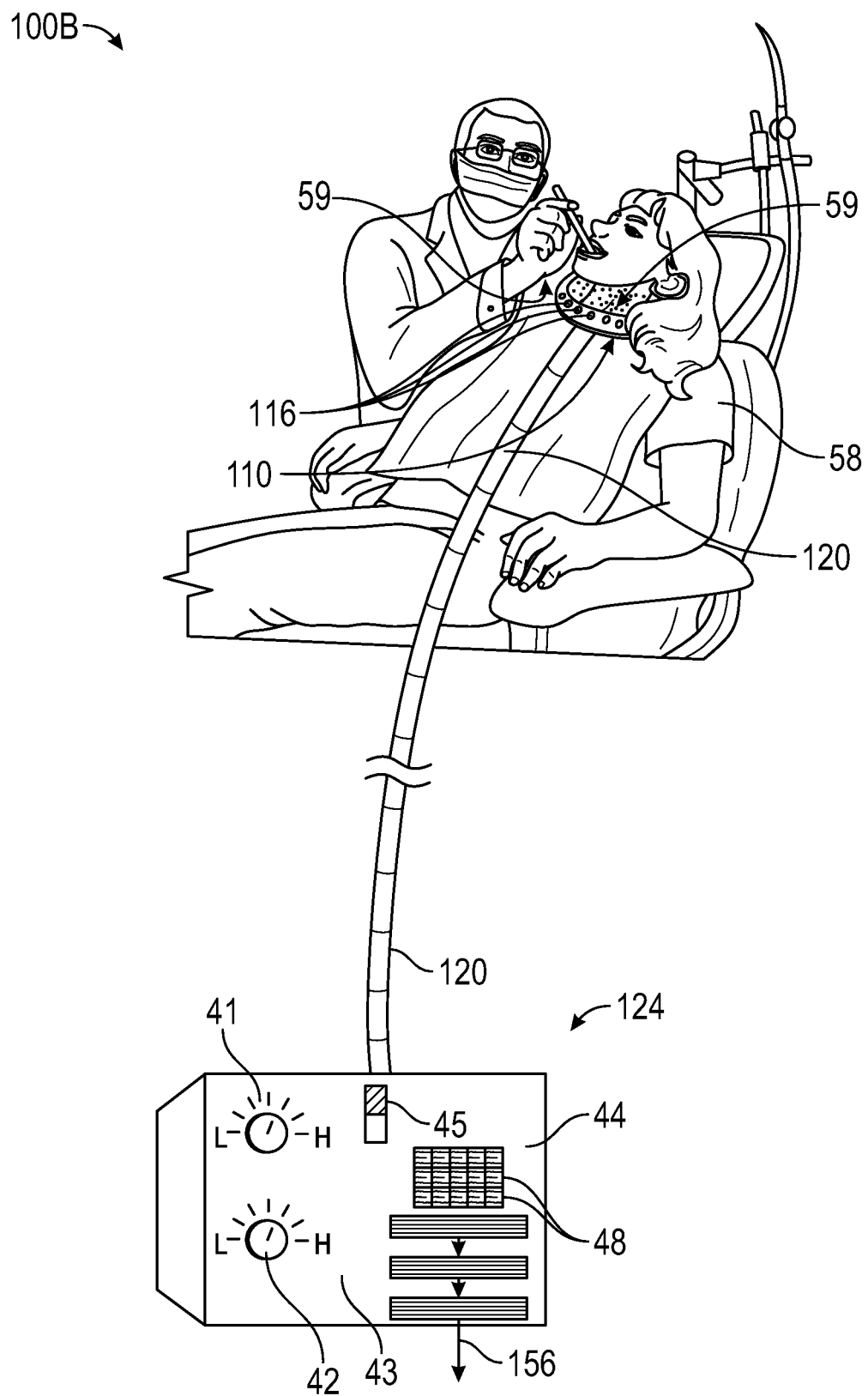
FIG. 3 shows an airborne pathogen extraction system in use during a dental procedure in accordance with the present disclosure.

Referring to FIG. 3, wherein like numerals represent like elements, an APES 100B in accordance with the present disclosure is shown in use during a dental procedure. The APES 100B includes an extraction nozzle ring 110, air hose 120 and air disinfection unit 124, which may be configured like the extraction nozzle rings 10A, 10B, 10C, 10D, 10E, air hose 20 and air disinfection unit 24 discussed above in connection with FIGS. 1A-1E and 2. During the dental procedure, a patient 58 wears the extraction nozzle ring 110 around their neck. Air extraction openings 116 are located on the extraction nozzle ring 110 near the mouth and nose of the patient 58 to maximize the air and potential pathogen/virus particles 59 being collected by the extraction nozzle ring 110 in that area. The air hose 120 connects the neck-worn air extraction nozzle ring 110 to the air disinfection unit 124, which may reside on the floor below the patient 58. This allows return airflow 156 from the air disinfection unit 124 to be directed along the floor and away from the dentist and/or dental hygienist. Such operation inherently limits the buildup of airborne pathogens within the general location of the patient that would potentially endanger subsequent patients as well.

Figure 4:
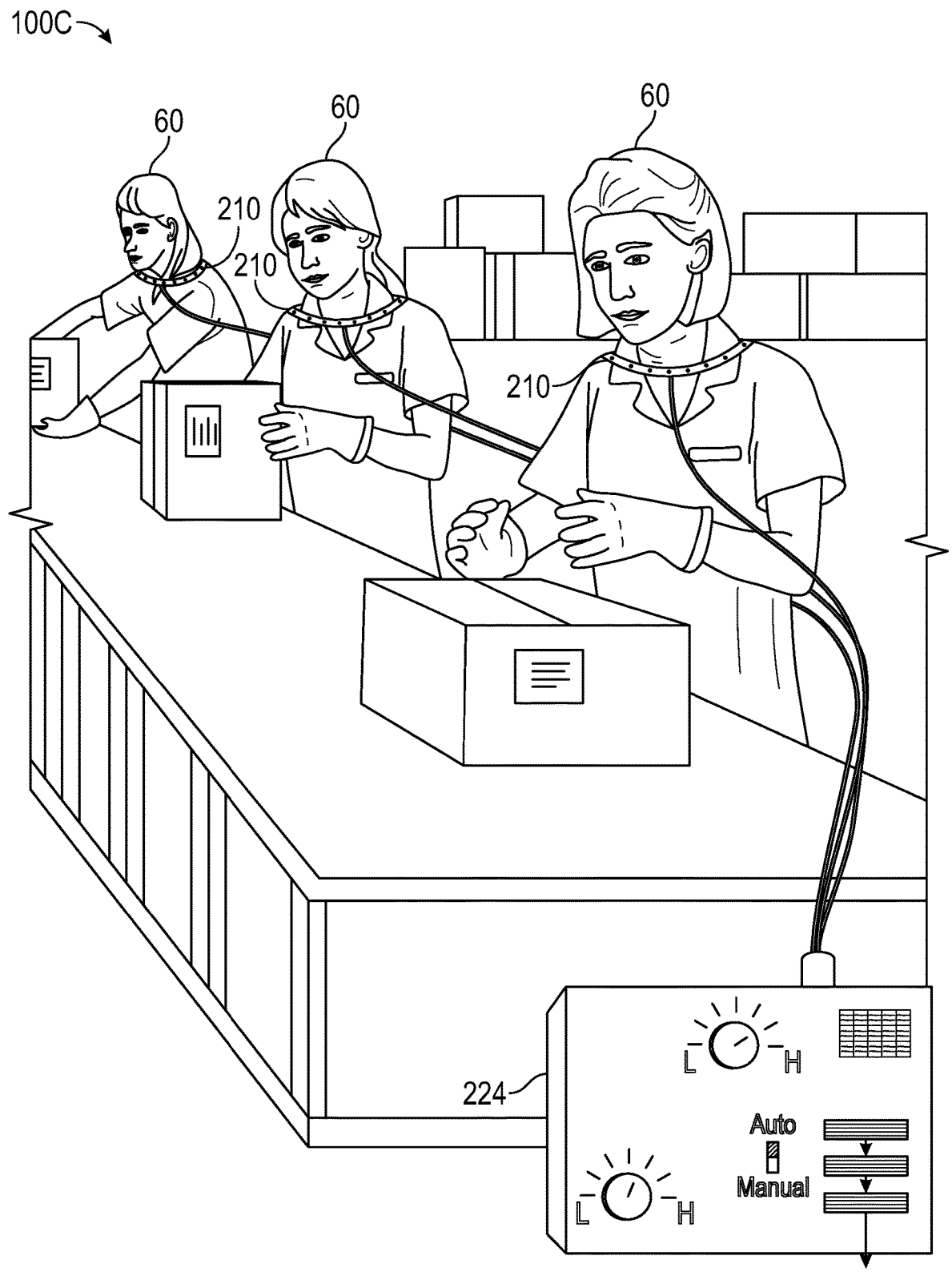
FIG. 4 shows an airborne pathogen extraction system with a plurality of extraction nozzle rings in use during an assembly line procedure in accordance with the present disclosure.

Referring to FIG. 4, another exemplary embodiment of an APES 100C in accordance with the present disclosure is shown in use during an assembly line procedure. In this embodiment, workers 60 are arranged in an assembly line fashion in close proximity to one another with each worker 60 wearing an extraction nozzle ring 210. While each worker 60 could be operatively connected to dedicated individual air disinfection units 24, 124 (FIGS. 2 and 3), in this embodiment the extraction nozzle rings 210 of the workers 60 are efficiently served by operatively connecting the plurality of extraction nozzle rings 210 to a larger or greater capacity single central air disinfection unit 24, 124. While the central air disinfection unit 24, 124 may filter and/or treat the airflow from the extraction nozzle ring 210 and return the air to the general area of extraction, in some embodiments, the air disinfection unit(s) 24, 124 may instead direct the airflow from the extraction nozzle rings 210 in an unfiltered (or untreated) manner to outside ambient air so any pathogens are diluted and spread out as well as the air is not locally returned to the same room or local environment of the workers 60 from which it was extracted.

Figure 5:
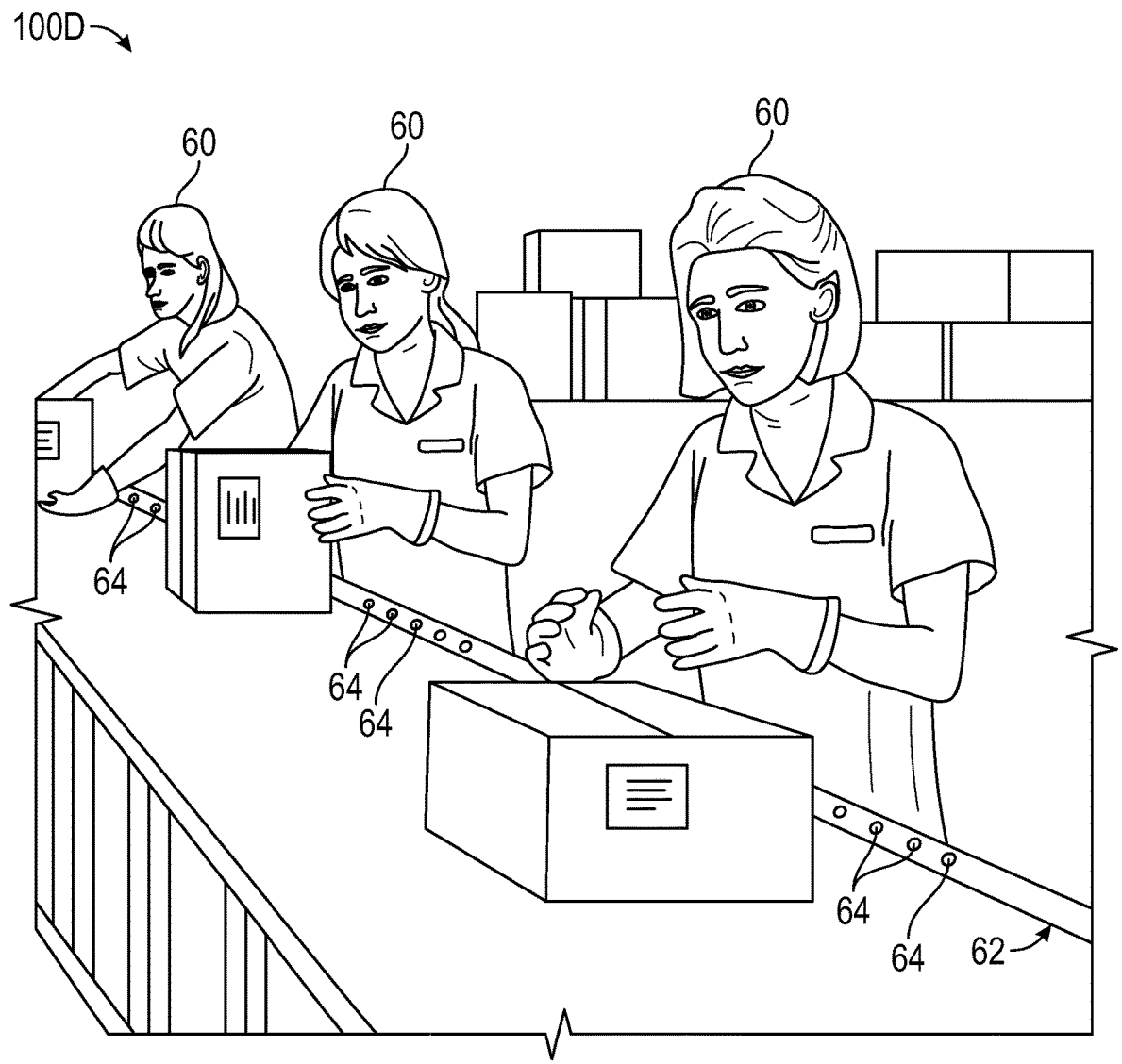
FIG. 5 shows an airborne pathogen extraction system with a fixed linear extraction nozzle in use during an assembly line procedure in accordance with the present disclosure.

Referring to FIG. 5, another exemplary embodiment of an APES 100D in accordance with the present disclosure is shown in use during an assembly line procedure. In this embodiment, a linear collection extraction nozzle 62 is used instead of providing extraction nozzle rings for all of the workers 60. The linear extraction nozzle 62 has a plurality of air extraction openings 64 strategically located proximate to each worker's 60 workstation position to optimize the collected airflow around each assembly line worker 60. The linear collection extraction nozzle 62 is connected to a central air disinfection unit 24, 124 of the APES 100D and operates to extract, and optionally filter and/or treat, air in the vicinity of the workers 60 in the same manner as APES 100A, 100B and/or 100C.

Figure 6:
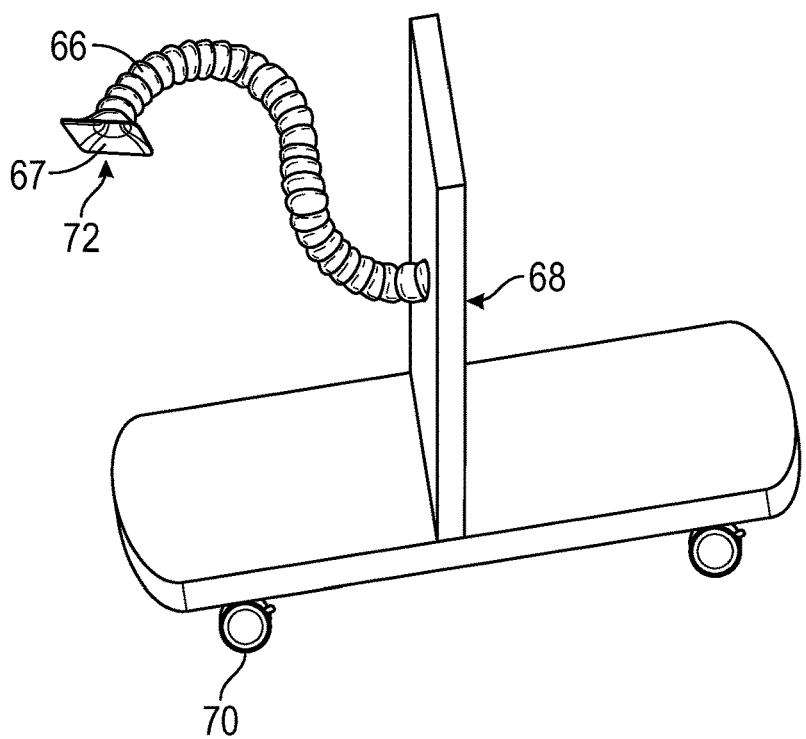
FIG. 6 shows an extraction nozzle connected to a rolling stand in accordance with the present disclosure.
Figure 7:
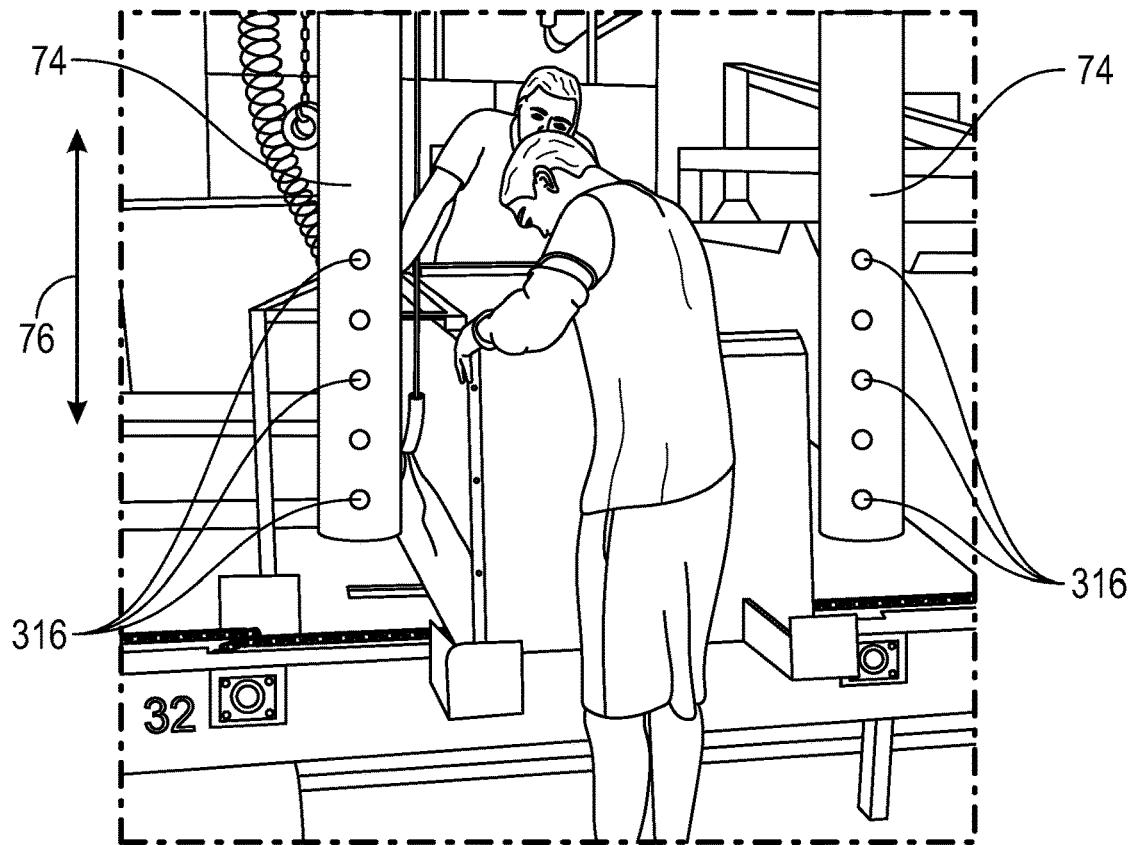
FIG. 7 shows vertically extending extraction nozzles in an environment of workers working in accordance with the present disclosure.

Advantageously, the APESs 100A, 100B, 100C, 100D in accordance with the present disclosure are able to capture and remove airborne virus particles and/or other airborne infectious pathogens 59 from ambient air that is proximate to an individual(s) who is actively shedding the virus particles from said individual's nose and mouth before the particles have a chance to move substantially away from the individual and infect other individuals. In some embodiments, the APES 100A, 100B, 100C, 100D may include an air extraction nozzle attached to a rolling stand, which is physically connected to flexible air hose 66. Referring to FIG. 6, an exemplary extraction nozzle 72 connected to a rolling stand 68 having a plurality of wheels 70 is shown in accordance with the present disclosure. The extraction nozzle 72 has a suction port 67 and is connected to an air disinfection unit (not shown) such as the air disinfection unit 24 shown in FIG. 2. The suction port 67 functions to receive air and airborne pathogens when an air flow generating means is working to generate negative air pressure in the extraction hose 66 as discussed above in connection with the air extraction openings 16 of FIGS. 1A-1E. The extraction hose 66 may be flexible or malleable so that the extraction nozzle 72 is positioned or articulated to rest at a certain location and/or direction to extract air and airborne pathogens. The air disinfection unit may be remotely located from the rolling stand 68 and/or extraction nozzle(s) 72, or may be incorporated as part of the rolling stand 68 assembly. Alternatively, rather than using a proximate area nozzle 72 as shown, a ring nozzle 10 (FIGS. 1A-1E) may also be used as well. The air output port of the air disinfection unit may include directional vanes or other means for directing the output air flow. In some embodiments, the output airflow is directed to the ground where gravity helps ensure any residual pathogen particles will remain. Optionally, HEPA, electronic, electrostatic (either passive or active), or other types of filter media may also be used in addition to UV light source treatment in order to capture the extremely small virus or other pathogens that survive light source treatment.

It should be readily understood that the extraction nozzle (s) of the APES 100A, 100B, 100C, 100D may be configured in different sizes and/or shapes to optimize various usage situations. For example and without limitation, the extraction nozzle rings 10 may be square-shaped, triangle-shaped, star-shaped, or elliptical-shaped or any other shape defining a central opening that fully encloses the central opening or partially encloses the central opening and is configured to be wrong around the neck of a user. Similarly, rather than a linear collection extraction nozzle 62, the collection extraction nozzle may be formed with an arc-shape, an s-curved shape, or any other similar shape to suite a desired application. Similarly, depending on airflow rate requirements, different sizes and/or lengths of flexible air hose may also be used.

The airflow generating means 25 of the air disinfection unit 24, 124 may include a blower assembly with a variable speed fan motor to allow the system's airflow rate to be adjusted and set to a selectable rate, such as a cubic feet per minute (CFM) target. A visual or digital CFM flow meter may optionally be provided on the air disinfection unit 24, 124 to assist in reaching a particular CFM goal or target. In some embodiments, a selector switch may be provided that enables one or more preset fan speeds to be selected. In some embodiments, the fan motor may have a fixed speed.

In operation, the extraction nozzle of the APES of the present disclosure is placed around the neck or proximate to a user, depending upon the desired application, and a highly flexible air hose connects the extraction nozzle(s) from one or more users to an air disinfection unit which may be portable and dedicated to a single hose and extraction nozzle, or to a central unit(s) capable of handling the needs of personnel arranged alongside an assembly line, meat packing plant, etc.

Figure 8A:
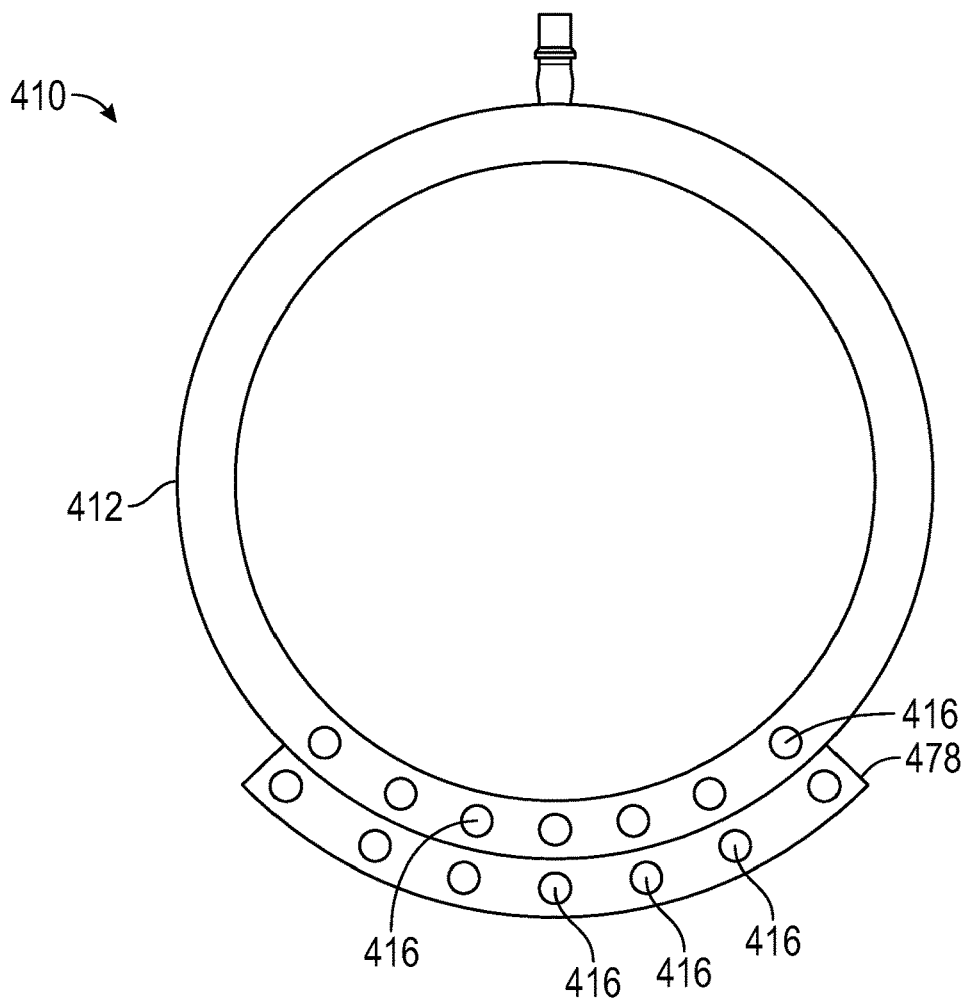
FIG. 8A shows a top view of an extraction nozzle ring in accordance with the present disclosure.
Figure 8B:
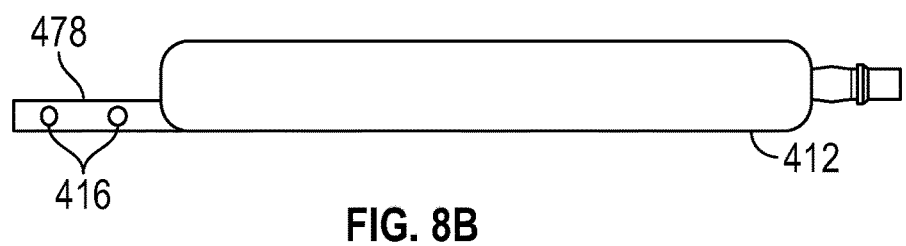
FIG. 8B shows a side view of the extraction nozzle ring of FIG. 8A in accordance with the present disclosure.
Figure 8C:
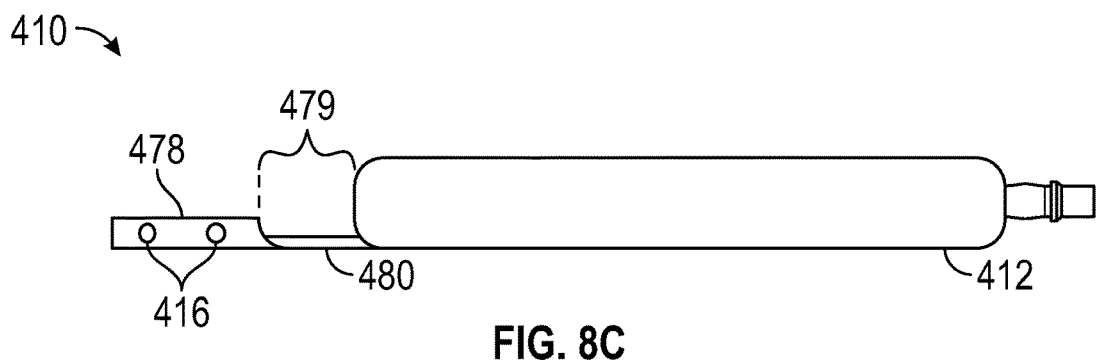
FIG. 8C shows a side view of the extraction nozzle ring of FIG. 8A with the lip extended in accordance with the present disclosure.

The APES generates a small area of negative pressure (relative to the general air pressure) in a given space in the vicinity of the extraction nozzle. Operationally this is similar to a smoke extraction system, but the APES of the present disclosure is designed to draw air into the extraction nozzle (s) in order to capture and remove any virus or other pathogen particles that are being emitted from a person through the nose and/or mouth contemporaneously with their emission so as not to let said particles become airborne and move a significant distance away from the emitting person. Once drawn into the air disinfection unit of the present system, the airflow is filtered either mechanically via passive electrostatic media filtration, via actively electrostatic media filtration, or via other types of HEPA filtration. Once the airflow moves beyond the filtration section, any remaining pathogen particles are subjected to the disinfecting light emission from the light source 44, which may be a high-intensity bombardment of UV-B light, UV-C light, or a combination of both UV frequencies. The intensity levels are calibrated to expose airborne pathogens to a level which renders them altered enough to prevent subsequent infection. The system has the ability to operate both with variable light intensities either by adjusting the intensity of the actual lamps or light sources, LEDS, etc. themselves, or by switching banks of emitters on or off to properly match a predetermined germicidal requirements at a given airflow rate, as well as offering variable airflow speeds achieved by either using variable speed motors and fans, and/or adjustable airflow dampers. Each APES described herein may be equipped with an airflow meter and chart to allow an operator to properly match a desired airflow rate with a needed or desired UV radiation level. Optionally, an automatic airflow rate/UV light intensity level system may be incorporated as well.

The filtered and disinfected air is intended to be outputted at a lower physical height dimension than the height that the air is drawn from into the extraction nozzle(s) in an effort to keep any pathogen from a user that survives the system away from the "T" zone of other parties, i.e. the part of the face that is made up of the eyes, nose, and mouth, and to keep any surviving pathogens that go through the system away from the "normal" room circulation airflow in order to minimize migration and to further keep said particles close to the floor where natural electrostatic attraction and gravity tends to keep airborne particles from rising.

As discussed above, the extraction nozzle ring may comprise a circular nozzle ring which is placed and worn around a user's neck. The extraction nozzle ring is used in conjunction with a lightweight and highly flexible air hose that is attached to the extraction nozzle ring and depending on need may be attached at various rotational angles around the user's neck. As such, the hose may be attached (typically at a downward angle) to the side or underside of the extraction nozzle ring either facing forward relative to the user, to the side of the user, or to the rear of the user. The extraction nozzle ring features an overall series of upward and/or downward facing air extraction openings which has the effect of creating a downward (relative to the user's nose and mouth) suction airflow that captures any emitted viruses/pathogens as soon as the virus/pathogen particles are expelled from the user's nose and/or mouth or soon thereafter. The diameters of individual air extraction openings may be different in size to other air extraction openings in the extraction nozzle ring, non-uniform opening spacing may be implemented, and the orientation of the air extraction openings may be adjusted as well in an effort to favor airflow from a certain location or direction.

In some embodiments, air extraction openings may not be present for the entirety of the extraction nozzle ring circumference, such as in the area behind a user's neck would for someone leaning back in a dentist's chair. Additionally, air extraction openings that are within the closest proximity to a user's nose and mouth may feature larger diameter openings and/or more closely spaced openings/density to increase or skew the extraction airflow in a targeted direction in order to better match the area of greatest extraction airflow with the outbreath that is being emitted by the user. The size and location of this increased airflow biasing may also be altered to allow for various nozzle designs that attempt to proportionally match and conform with the expected amount of a user's side to side head swivel movement/head rotation relative to the type of their work, conversation or communication levels with co-workers, etc. For ease of extraction nozzle ring placement and removal from a user, variations on the design of the extraction nozzle ring may include incorporating removable sections of the body of the extraction nozzle ring which press-fit together to allow easier nozzle placement and removal by removing and replacing a section of the ring from another.

As discussed above, in some embodiments, an extraction nozzle may be mounted on a stand. The stand may be equipped with one or more wheels to allow the stand and attached extraction nozzle to be conveniently moved to a desired spot or location. The stand may be equipped with a height adjusting mechanism which allows a desired height of the extraction nozzle to be set. Optionally, the stand may also feature an extraction nozzle and hose attached to an articulated arm assembly mechanism for further spatial adjustment.

In some embodiments, the extraction nozzles may include perforated air tubes that hang vertically between workers, optionally with hanging air curtains providing enhanced individual isolation, which may be particularly suitable for assembly line procedures or other procedures with users in close proximity to one another in a line or other formation. Referring to FIG. 7, shows vertically extending hanging extraction nozzles 74 in accordance with the present disclosure. The extraction nozzles 74 extend in a vertical direction 76 and each define a plurality of air extraction openings 316. The extraction nozzles 74 connect to an air disinfection unit (not shown) similar to the air disinfection unit 24 shown in FIG. 2. The air extraction openings 316 function to receive air and airborne pathogens when an air flow generating means is working to generate negative air pressure in the area of extraction nozzle 74 as discussed above in connection with the air extraction openings 16 of FIGS. 1A-1E. The extraction nozzles 74 may be fixed adjacent to where a work would stand while working. The layout, number and orientation of the air extraction openings 316 would be fixed and correspond to the specific needs of the work being performed. The air extraction openings 316 may be clustered and arranged at head-height, with one extraction nozzle 74 arranged in pairs on opposite sides of a worker's head. The rotational orientation of the air extraction opening perforations would be designed to correspond with the location of the workers. Alternatively, or in addition, individual nozzles in a linear fashion may be placed in a horizontal orientation generally in front of each worker along the edge of an assembly line. As an alternative to individual nozzles being used in conjunction with an assembly or production line, as shown in FIG. 5, a single extraction tube may extend laterally passing by numerous workers, but the air extraction perforations of those tubes may only be present in the general area of each worker.

Referring to FIGS. 8A-8C, an exemplary extraction nozzle ring 410 is shown in accordance with the present disclosure. The extraction nozzle ring 410 has a body 412 connected to a lip 478 (or deflector). The body 412 and lip 478 each include a plurality of extraction openings 416. The lip 478 is configured to slidably extend outward from the body 412 from a proximal (e.g., retracted) position shown in FIG. 8B to a distal (e.g., extended) position shown in FIG. 8C. A gap 479 is formed between the lip 478 and the body 412 when the lip 478 is in the distal position. The extension of the lip 478 to the distal position further shapes and optimizes an extraction airflow in a targeted direction through extraction opening 416 location, extraction opening 416 separation distance, extraction opening 416 shape and/or extraction opening 416 density. A person of ordinary skill in the art would be able to appreciate that the overall resulting extraction airflow direction and/or strength is dependent on the configuration of the plurality of extraction openings 416 and level of the suction force being generated by the APES. The lip 478 maintains fluid connectivity to the body 412 by the use of a "slip ring" through which a section of ducting allows the lip 478 to slide relative to the body 412 between the proximal position and the distal position. Said ducting maintains a fluid connection to an inner volume of the body 412 through one or more sliding duct sections 480. Each sliding duct section 480 may be a unitary body, or may be a plurality of concentric tubes in order to function as a telescoping sliding duct section 480. However, a fluid connection from the main body 412 to the lip 478 may be through a fluid connection of any extension element(s). The lip 478 is continuously adjustable between at least two positions, such as the proximal position shown in FIG. 8B and the distal position shown in FIG. 8C. The extraction nozzle ring 410 is configured to connect to an air hose of an APES 100, 200, 300, 400, 500 discussed above through a connector, which is discussed in greater detail later herein.

The ability of the lip 478 to be adjusted or operationally extended in the field may also be for an enhanced increase in the capture of liquid emanations from a user's mouth occurring under different use applications, such as during a dental procedure at a dentist office or the like. The ability of the lip 478 to be adjusted or extended to the distal position also allows for better capture of droplets expelled from the user during or after a cough, sneeze, during times of increased exhalation such as singing, or other times when the user is wearing the extraction nozzle ring 410 with the lip 478 in the distal position in order to better match the projection of exhalation and/or droplets.

In some embodiments, the lip 478 is integral with the body 412 and forms a portion of the ring shape of the extraction nozzle ring 410. As previously described in connection with other extraction nozzles, the nozzle shape, extraction opening distribution locations, extraction opening size, etc. are determinant of air flow extraction shaping. Enhanced air extraction in a specific direction or targeting a specific area (or volume) when the extraction nozzle is worn or near a user can be accomplished with a slidably extending lip 478 as discussed above, or with an integral lip as an inherent part of the ring itself in order to provide a particular extraction function for a targeted area (or volume) or for a particular air flow direction. The integral lip may not be extendable, but forms a portion of the shape or ring shape of the extraction nozzle. Thus, an extraction nozzle may still be ring shaped and include a lip or appendage for a desired extraction function for a specific application of an APES or extraction nozzle.

Figure 9A:
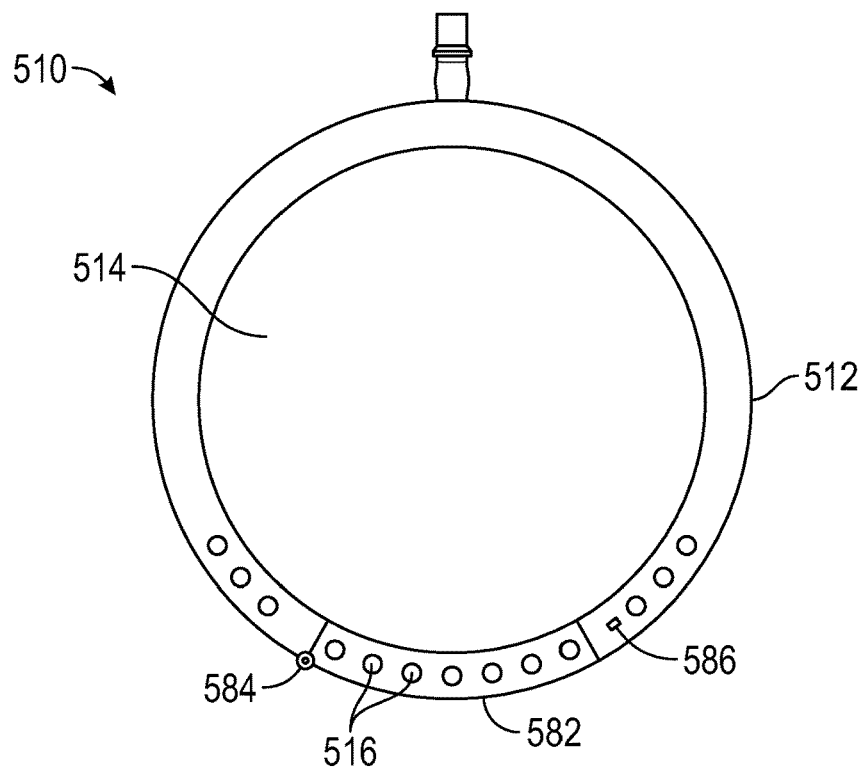
FIG. 9A shows a top view of an extraction nozzle ring in a closed position in accordance with the present disclosure.
Figure 9B:
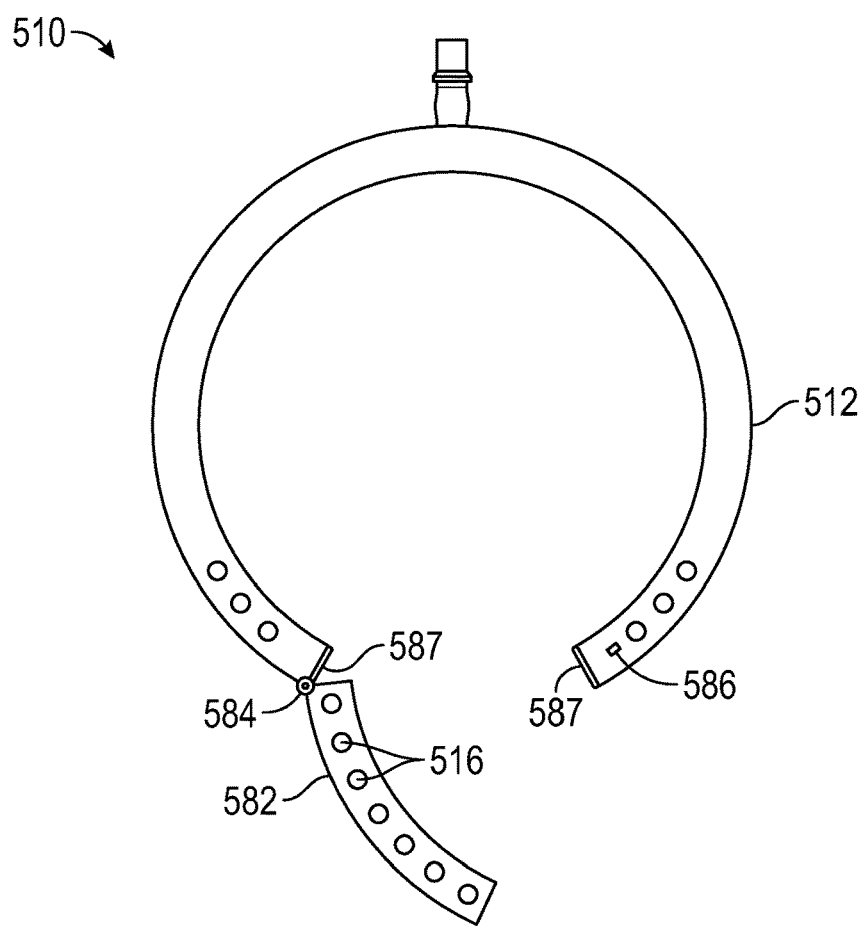
FIG. 9B shows a top view of the extraction nozzle ring of FIG. 9A in an open position in accordance with the present disclosure.

Referring to FIGS. 9A and 9B, an exemplary extraction nozzle ring 510 is shown in accordance with another embodiment of the present disclosure. The extraction nozzle ring 510 has a body 512 and a movable section 582 connected to the body 512 through a hinge 584 located at one end of the movable section 582. The body 512 includes a latch 586 configured to lock and unlock a second, free end of the movable section 582 to the body 512. The second, free end of the movable section 582 is the end opposite the end of the movable section 582 hingedly connected to the body 512. The body 512 and/or movable section 582 define air extraction openings 516 fluidly connected to an inner volume of the body 512 as discussed above in connection with other extraction nozzle embodiments. The extraction nozzle ring 510 includes a gasket 587 located at the interface between the body 512 and the movable section 582 at the end of the movable section 582 that is hingedly connected to the body 512. The gasket 587 is a soft gasket, rubber gasket, or the like, and is configured to ensure an airtight connection of an inner volume of the movable section 582 to an inner volume of the body 512 at the interface. A gasket 587 may also be provided at the interface between the second, free end of the movable section 582 and the body 512 to provide for a better air seal. The gaskets 587 may be formed by providing gasket material on both ends of the movable section 582, both ends of the body 512 facing the ends of the movable section 582, or any combination of ends of the movable section 582 and/or ends of the body 512 facing the ends of the movable section 582. The extraction nozzle ring 510 is configured to connect to an air hose of an APES 100, 200, 300, 400, 500 discussed above through a connector, which is discussed in greater detail later herein.

In operation, a user activates the latch 586 to unlock the movable section 582 from the body 512. Then, the user moves the movable section 582 from the closed position shown in FIG. 9A to the open position shown in FIG. 9B. The user may then insert their neck into the central opening 514 of the extraction nozzle ring 510 through the opening in the ring provided by moving the movable section 582 to the open position. The movable section 582 may then be returned to the closed position shown in FIG. 9A. In the closed position, the latch 586 engages the movable section 582 to lock the free end of the movable section 582 to the body 512.

The hinged movement of the movable section 582 allows for the extraction nozzle ring 510 to fit around the neck of a user even if the central opening 514 of the extraction nozzle ring 510 is too small to fit over the user's head, as long as the central opening 514 is large enough to fit around the user's neck. The latch 586 may be configured as according to any known latching mechanism or locking/engagement structure(s) known in the art.

Figure 10A:
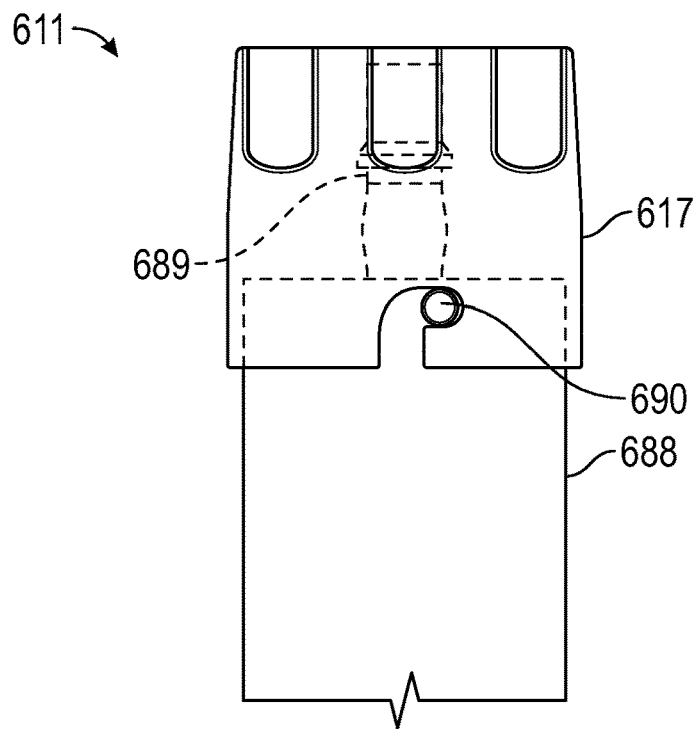
FIG. 10A shows a side view of bayonet type valve opening connectors in accordance with the present disclosure.
Figure 10B:
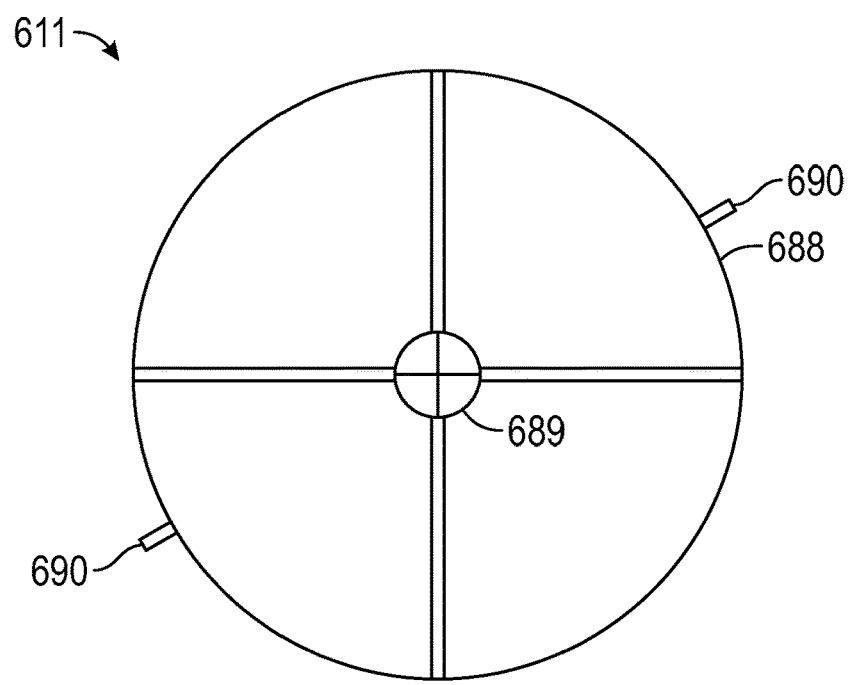
FIG. 10B shows a top view of a connector of FIG. 10A connectors in accordance with the present disclosure.

Referring to FIGS. 10A and 10B, a bayonet type automatic inlet valve opening connector 611 with a corresponding female connector 617 are shown in accordance with the present disclosure. The connector 611 includes a main body 688 having an opening pin 689 and bayonet pins 690. The opening pin 689 is configured to be inserted into and open a corresponding female valve connector. The connector 611 is configured to be used with any of the extraction nozzles within the scope of the present disclosure for connecting the extraction nozzles to an air hose. An extraction nozzle comprising the connector 611 provides for a connection that automatically closes and seals off airflow into one end of an air hose should the extraction nozzle become disconnected or if the air hose is without an extraction nozzle (e.g. any of the extraction nozzle rings discussed herein). The connection at the other end of the air hose (i.e. the end connected to the air disinfection unit) may be similarly configured to automatically close and seal off airflow through the connector if the air hose is removed from the air disinfection unit to ensure efficacy of the APES in case the air hose is removed. Connectors 611 including other attachment mechanisms besides the bayonet pin-type connection are within scope of the present disclosure. For example, and without limitation, push-in slip fit attachment mechanisms that utilize a spring-loaded connector may be used to ensure a tight fit. Additionally, less secure attachment mechanisms may be used for the connector since the suction nature of the air flow inherently tends to hold parts of the system together, in contrast to a central pressurized air system that would put strain on connection point and, thus, require more secure attachment mechanisms.

The bayonet type automatic inlet valve opening connector 611 provides a simple and easy to use connection system for connecting extraction nozzles and air hoses. Thus, each seating position in an entire row, section, or facility for every seat may be provided with an air hose operably connected to one or more air disinfection units through a manifold, thereby providing extraction capability. However, only extraction nozzles actually connected to one of the air hoses through a connectors 611 would be functionally connected to an air disinfection unit operably connected to the manifold. Since, at any given time, any seat (or workstation) may not be occupied, the bayonet type automatic inlet valve opening connectors 611 allow unnecessary parasitic pressure losses within the system to be avoided by disconnecting suction from those unoccupied positions. Similarly, the connections between an air manifold or linear extraction pipe or tube and individual air hose(s) may also be equipped with an automatic sealing junction or connection, thereby allowing the air hose(s) to be removed without introducing unnecessary parasitic pressure losses. When attaching an air extraction nozzle to the connector valve at the end of an air hose, the extraction nozzle (or other extraction device) would physically push open an inlet valve and be made operationally functional by a physical protrusion, such as the opening pin 689, within the air hose connector from the extraction nozzle having such a connector 611. Similarly, when an air hose would be inserted into a connector attached to a manifold (or other main line) piping, the hose end would physically enable that particular fluid connection path between an individual air hose and the connected aggregation piping or tube. In some embodiments, the connectors may be reversed, i.e. the air hose includes the male connector 611 and the extraction nozzle includes the female connector with sealing member that seals when the male connector 611 is not connected.

Figure 11:
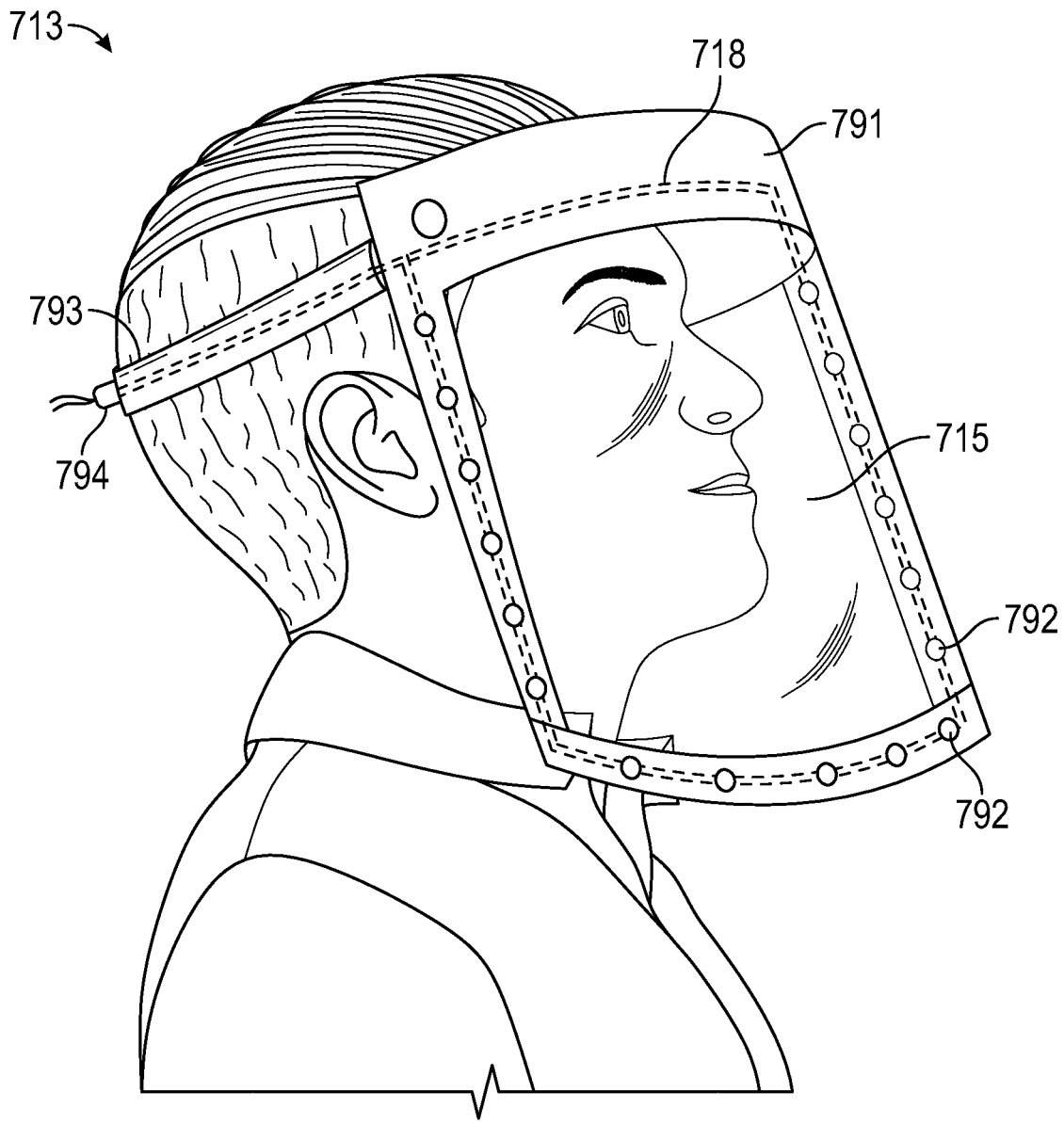
FIG. 11 shows an extraction nozzle face shield in accordance with the present disclosure.

Referring to FIG. 11, an extraction nozzle face shield 713 is shown in accordance with the present disclosure. The face shield 713 includes a main body 791 having a hollow interior area containing a fluid section possessing an inner volume 718 and a plurality of air extraction openings 792 formed therethrough that are fluidly connected to the inner volume 718. The plurality of air extraction openings 792 are arranged about a central transparent or translucent shield element 715. The inner volume 718 is fluidly connected to a connection tube 793. The connection tube 793 is connected to an air hose connector 794, which is configured to connect to an air hose of an APES 100, 200, 300, 400, 500 discussed above. The connector 794 may be, for example, the connector 611 of FIG. 10A. The extraction nozzle face shield 713 operates to extract airborne pathogens similar to the extraction nozzle rings 10, 110, 210 disclosed herein and, thus, a repeat of the extraction process is not necessary. The air extraction openings 792 may be configured to target a desired direction of airflow extraction in a similar manner to that described herein in connection with the extraction nozzle rings.

By integrating air extraction into the extraction nozzle face shield 713, a user that requires or desires to wear a face shield and an extraction nozzle ring advantageously does not need to wear two different pieces of personal protective equipment. The integrated design of the extraction nozzle face shield 713 serves to provide both the protection of a face shield and the airborne pathogen extraction functionality of an extraction nozzle. Further, the extraction nozzle face shield 713 may have reduced fogging as compared to a conventional non-extraction type face shield due to the extracted moist airflow generated by an air disinfection unit operatively connected to the face shield 713.

Figure 12:
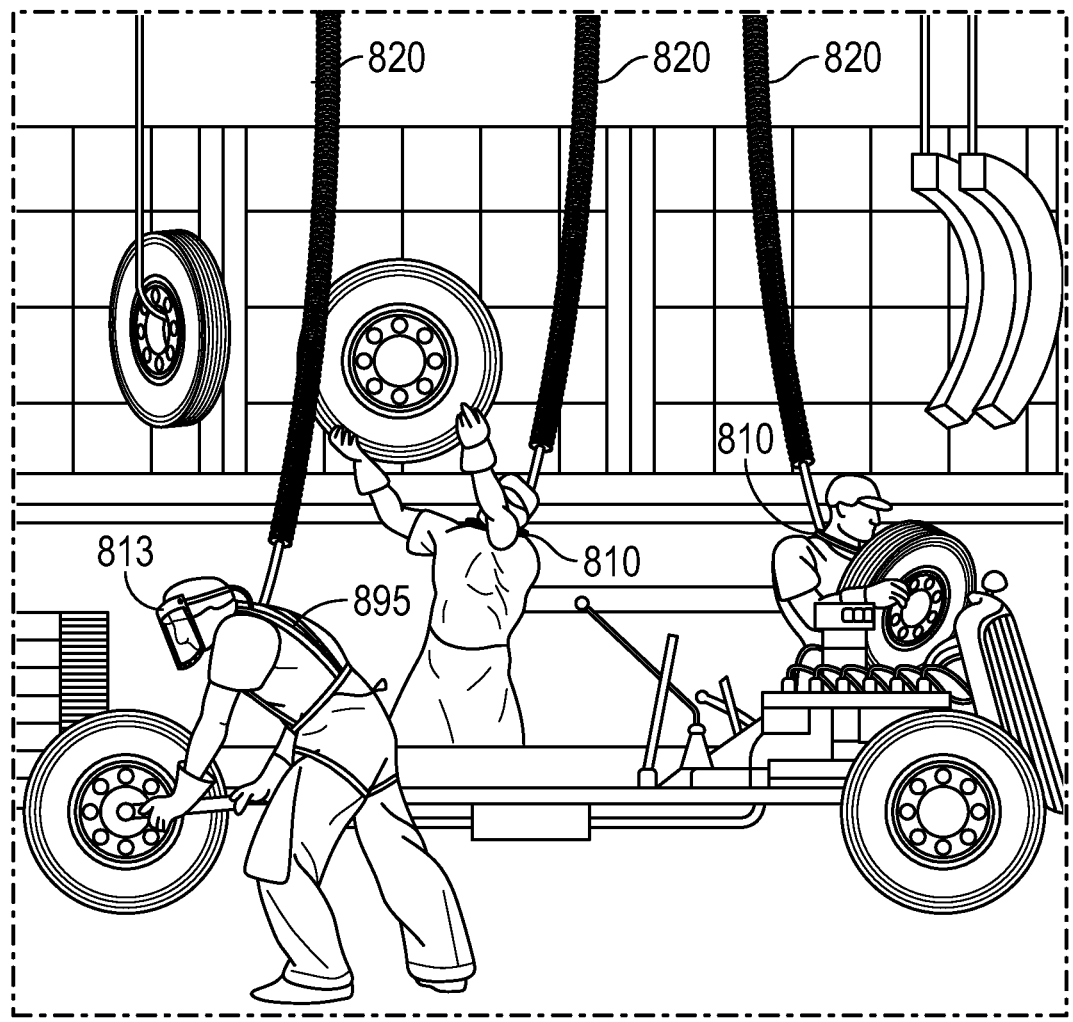
FIG. 12 shows an airborne pathogen extraction system with overhead hanging coiled air hoses in accordance with the present disclosure.

Referring to FIG. 12 an airborne pathogen extraction system with overhead hanging air hoses 820 is shown in accordance with the present disclosure. The air disinfection unit is not shown for convenience, but may be arranged overhead where the air hoses 820 connect or elsewhere. Two of the overhead hanging air hoses 820 are connected to extraction nozzle rings 810 of two users. One of the overhead hanging air hoses 820 is connected to an extraction nozzle face shield 813. The overhead hanging air hoses 820 may be directly connected to the extraction nozzle rings 810 and/or extraction nozzle face shield 813, or may optionally be physically connected to a body harness 895, but still fluidly connected to the face shield 813 or extraction nozzle ring 810, to better allow the air hose 820 to naturally move with the user. The overhead hanging air hose 820 allows for movement of the user of the connected extraction nozzle within an area determined by a length of the overhead hanging air hose 820 and/or position of the air disinfection unit to which the air hose 820 is connected. While the overhead hanging air hoses 820 are shown as being coiled in a helically wound spring configuration, in some embodiments the overhead hanging air hoses 820 may not be coiled, e.g. the overhead hanging air hoses 820 may be flexible overhead hanging air hoses that do not have any particular shape memory.

Referring to FIG. 13A, an axial cutaway section of an air duct 996A of an APES, such as the APES 100, 200, 300, 400, 500 discussed above, is shown in accordance with the present disclosure. The air duct 996A includes an extended dwell time ultra-violet ("UV") irradiation system having a UV light source 997A (e.g., a UV-B or UV-C light source) mounted in a radially central location of the air duct 996A through mounts 998A. The UV light source 997A has a longitudinal extension in an axial direction 999 of the air duct 996A. The axial direction 999 is the general direction of air flow within the air duct 996A when the APES is in operation. The UV light source 997A is configured to generate and emit UV light with 360° of radial coverage. The air duct 996A further includes a pressure sensor and/or flowrate sensor 1000 configured to detect a pressure and/or flowrate of air flow within the air duct 996A. The pressure sensor 1000 is configured to transmit detected pressure and/or flow rate data to a controller of the APES through a wired or wireless data connection.

Figure 13C:
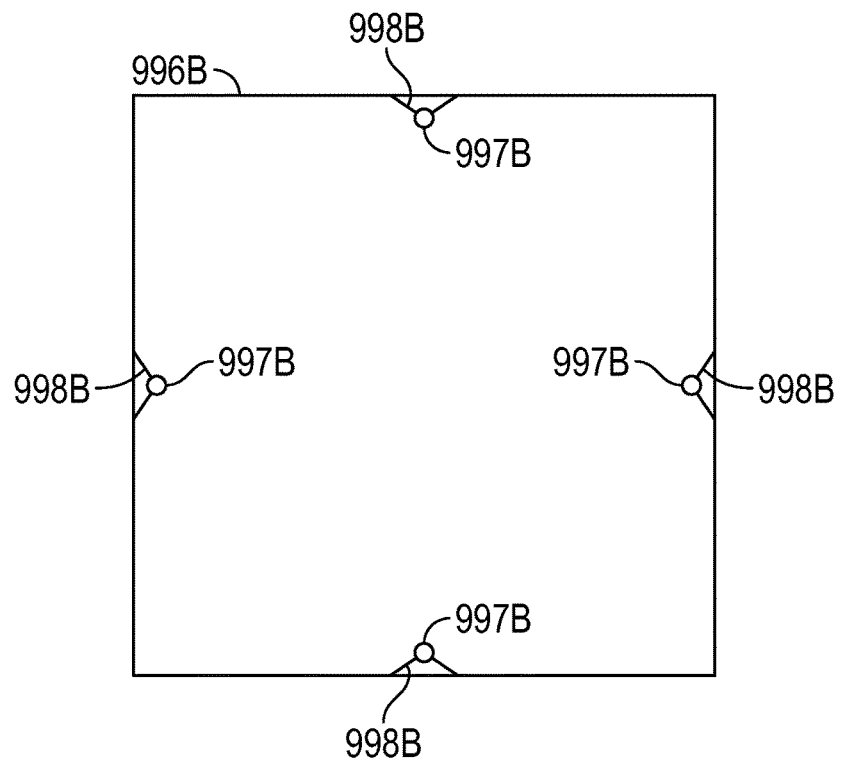
FIG. 13A shows an axial cutaway section of an air duct in accordance with the present disclosure.

Referring to FIGS. 13B and 13C, an axial cutaway section and a radial cutaway section, respectively, of another air duct 996B of an APES, such as the APES 100, 200, 300, 400, 500 discussed above, is shown in accordance with the present disclosure. The air duct 996B includes an extended dwell time UV irradiation system having a plurality of UV light sources 997B (e.g., UV-B or UV-C light sources) mounted in radially lateral locations of the air duct 996B through mounts 998B. The light sources 997B are arranged at radial lateral top, left, bottom and right locations of the air duct 996B. The UV light sources 997B each have a longitudinal extension in an axial direction 999 of the air duct 996B. The axial direction 999 is the general direction of air flow within the air duct 996B when the APES is in operation. The air duct 996B further includes a pressure sensor and/or flowrate sensor 1000 configured to detect a pressure and/or flowrate of air flow within the air duct 996B. The pressure sensor 1000 is configured to transmit detected pressure and/or flow rate data to a controller of the APES through a wired or wireless data connection.

Figure 13D:
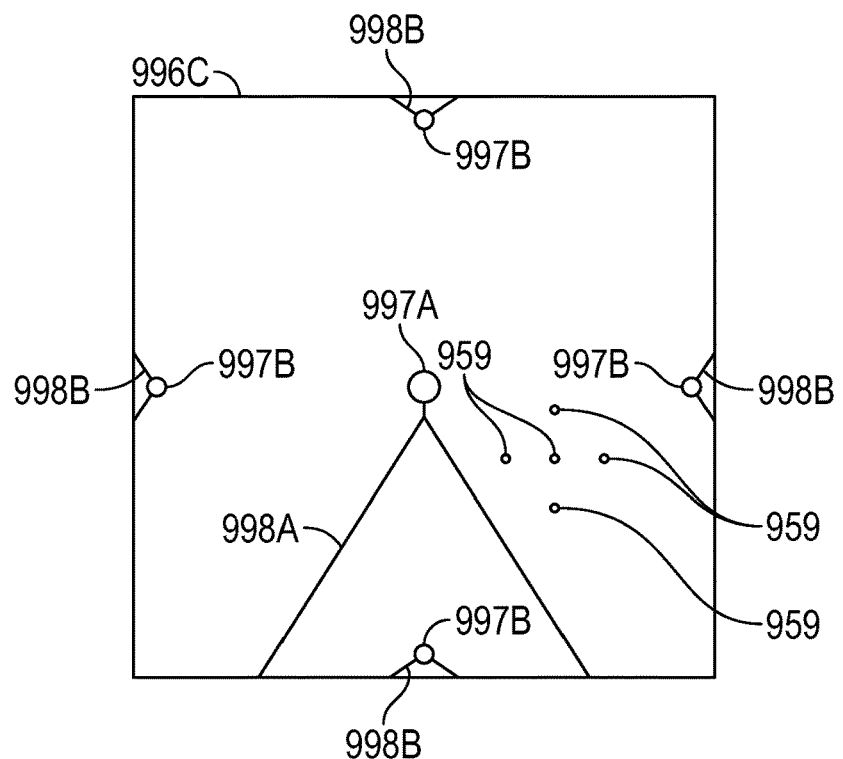

Referring to FIG. 13D, a radial cutaway section of an air duct 996C of an APES, such as the APES 100, 200, 300, 400, 500 discussed above, is shown in accordance with the present disclosure. The air duct 996C is a combination of the air ducts 996A and 996B of FIGS. 13A and 13B, respectively. Specifically, the air duct 996C includes an extended dwell time UV irradiation system having a UV light source 997A (e.g., a UV-B or UV-C light source) mounted in a radially central location of the air duct 996C through mounts 998A. The UV light source 997A has a longitudinal extension in an axial direction 999 (see e.g. FIGS. 13A and 13B) of the air duct 996C. The UV light source 997A is configured to generate and emit UV light emissions with 360° of radial coverage. The axial direction 999 is the general direction of air flow within the air duct 996C when the APES is in operation. The UV irradiation system shown in FIG. 13D further includes a plurality of UV light sources 997B (e.g., UV-B or UV-C light sources) mounted in radially lateral locations of the air duct 996C through mounts 998B. The UV light sources 997B each have a longitudinal extension in the axial direction 999 of the air duct 996C. Potential pathogen/virus particles 959 are shown for illustrative purposes as being carried by the air flow through the air duct 996C. As the pathogen/virus particles 959 pass through the air duct 996C, the pathogen/virus particles 959 are irradiated by the UV light emitted by the UV light sources 997A, 997B.

In APES embodiments that are designed to return filtered and disinfected air to the general originating area, some embodiments may be configured with one or more air ducts, such as the air ducts 996A, 996B, 996C of FIGS. 13A-13D. A disinfecting air duct 996A, 996B, 996C may provide a high "dwell time" for pathogenic material that is transiting through a disinfecting area of the air ducts 996A, 996B, 996C (i.e. the portion/section of the duct 996A, 996B, 996C irradiated by a UV light source(s)) in order to ensure a high degree of efficacy. Conventional UV lights (e.g. UV-B or UV-C lights) are oriented perpendicular to air flow in air disinfecting systems. However, the UV light sources 997A, 997B of the air ducts 996A, 996B, 996C have their longitudinal extensions in the direction of air flow (i.e. the axial direction), thereby increasing UV light exposure time of pathogens passing through the air ducts 996A, 996B, 996C and likelihood of disinfection of the pathogens. Therefore, APES embodiments of the present disclosure advantageously provide for a higher cumulative dosage of radiation by dramatically increasing the amount of transit time during which pathogenic particles are exposed to UV radiation (i.e. "dwell time"), as well as critically provide a superior total angular surface coverage for each pathogenic particle. The disinfection light sources of the present disclosure being mounted lengthwise and parallel to air flow, as well as arranging the light sources in the center and/or lateral locations of the air duct provide for superior disinfection functionality. Multiple center and lateral UV light sources 997A, 997B may be used in successive, parallel, or a combination of both in order to increase the amount of disinfection emission that pathogens receive per pass through the air duct 996A, 996B, 996C. Any frequency or type of UV light or known pathogen disinfecting light may be used for the light sources 997A, 997B.

In some embodiments, in order to maintain a desired negative air pressure within a system of simultaneously connected extraction nozzles that are fluidly connected to a central air extraction system (or central air disinfection unit(s)) or its manifold(s) for the purpose of providing sufficient extraction capability as well as to maintain a suction pressure that minimizes operational noise creation, one or more pressure sensors 1000 may be operatively connected to a controller of the system to provide for feedback based control during operation of the system. The controller may be configured to operate the suction generating means (e.g. one or more fan drives) in order to monitor, optimize, and/or compensate for the total number of extraction nozzles that are in operative use at any given time based on input received from the one or more pressure sensors. As the number of extraction nozzles in use increases or decreases, the net addition or subtraction of the extraction nozzles may alter the system suction pressure in a particular sectional area or in the system as a whole (or both), and the pressure sensors, which are operatively connected to a variable frequency drive (VFD) compensate for the changing system suction pressures in order to maintain a desired target internal extraction pressure throughout the system. The system may also maintain a desired pressure in situations where aggregated sections of the system may be dynamically connected or disconnected. This would allow entire rows of seats or sections to be shut off if not needed.

The controller is configured to control the air disinfection unit to generate a predetermined level of negative air pressure based on a number of extraction nozzles connected to the system and in use, as determined based on data provided to the controller by the one or more pressure sensors. For example, the controller may be configured to control the air disinfection unit to generate the predetermined level of negative air pressure by operatively controlling a variable frequency drive of an airflow generating mean. Further, the controller may be configured to control the air disinfection unit to generate a high negative air pressure when the controller determines that a number of the plurality of extraction nozzles in use is above a first threshold, and control the air disinfection unit to generate a low negative air pressure when the controller determines that the number of the plurality of extraction nozzles in use is below a second threshold.

In some embodiments, the extraction nozzles described herein may be provided with baffling within the air flow path or inner volume in order to alter the sound characteristics of air flowing into the air extraction openings. For example, baffling may be arranged in proximity to the air extraction openings to eliminate or reduce sounds generated by air flowing into the extraction nozzle from reaching an ear of a user using the extraction nozzle. The sound alteration may reduce the user perceptible sound level, frequency of the user perceptible sound level, or other bothersome audible characteristics of the extraction nozzle while air flow is flowing into the extraction nozzle. In some embodiments, sound absorbing material, such as loose spin material (or other fibrous sound mitigating material that allows a majority of air to flow past while reducing sound) that may be used internally of the extraction nozzle to achieve sound level or sound type mitigation. The sound absorbing material may be arranged in the nozzle body of the extraction nozzle and/or in the lip of the extraction nozzle. Depending on the size and number of air extraction openings, as well as the type of extraction nozzle (e.g. extraction nozzle ring, or extraction nozzle face shield, etc.), as well as the use environment (theater, factory floor, etc.), the method, materials, designs may change to suit the particular application.

In some embodiments, the APES may be implemented in a theater or other seated venue, wherein each seat would be provided with an extraction ring and air hose which would be fluidly connected to a distribution manifold which may run linearly beneath a row of seats and be connected to a central air extraction system for filtering and sterilization, or directed unfiltered to the outside air. Optionally, if the APES directly dumps the extracted air outside of a facility, an Energy Recovery Ventilator (ERV) may be used to supply makeup air from a different location of the outside to make up for a volume of extracted air in an energy efficient manner.

In some embodiments, the APES may be implemented in a passenger aircraft, each seat would have an extraction nozzle ring fluidly connected via an air hose to a distribution manifold located under each row of seats, which would subsequently be fluidly connected to the return air ducts of the airplane where it would be filtered by the existing HEPA filters and then treated with UV light before being re-introduced to the aircraft's cabin.

In some embodiments, the APES may be implemented by personnel needing to move between physical locations, a portable (carry-able) embodiment would be used wherein the air treatment unit would have a shoulder-strap that would keep the system in proximity to the user and function as the user moved between various positions.

In the case of a large industrial environment, the aggregated filtered and disinfected output of the building's APES may discharge to the outside air so as to minimize or not add to airflow within a structure, further limiting the spread of any errant virus/pathogen particles within the building or structure.

In some embodiments, such as in a hospital or healthcare setting, an optional hanging area hood with side curtains or collapsible frame tent may be used with the APES to further isolate an individual(s) without having to depend on overall negative air pressure room use.

In a setting such as a public restaurant, an extraction ring may run under a table at the table edges, or may be located in the center of the table to create an extraction airflow from people seated at each table, thus minimizing the infection possibility to patrons at adjacent tables. In another embodiment of this system, a circular manifold tube attached to the underside of the table with air inlets strategically located around the table circumference, short air hoses with extraction rings would be able to be attached to said manifold and allow diners to enjoy their food and drinks without the obstruction of a face mask.

While the present disclosure has been illustrated and described with respect to particular embodiments thereof, it should be appreciated by those of ordinary skill in the art that various modifications to this disclosure may be made without departing from the spirit and scope of the present disclosure.

What is claimed is:

1. An airborne pathogen extraction system comprising:
an extraction nozzle having a nozzle body and a lip, the nozzle body and/or the lip defining a plurality of air extraction openings fluidly connected to the inner volume of the nozzle body; and
an air disinfection unit fluidly connected to the inner volume of the extraction nozzle through an air hose;
wherein the air disinfection unit is configured to generate negative air pressure in the air hose to cause air to flow from an exterior of the extraction nozzle through the plurality of air extraction openings, into the inner volume of the nozzle body, into the air hose, and then to the air disinfection unit; and
wherein the lip is configured to move away from the nozzle body.

2. The airborne pathogen extraction system according to claim 1, wherein the lip is adjustable from a proximal position near the nozzle body to a distal position that is farther from the nozzle body than when in the proximal position.

3. The airborne pathogen extraction system according to claim 1, wherein the nozzle body and/or the lip comprises a sound absorbing material.

4. The airborne pathogen extraction system according to claim 3, wherein the sound absorbing material is a spun material.

5. The airborne pathogen extraction system according to claim 1, wherein the extraction nozzle comprises one or more baffles to eliminate or reduce sounds generated by air moving through the extraction nozzle from reaching an ear of a user of the extraction nozzle.

6. The airborne pathogen extraction system according to claim 1, wherein the extraction nozzle has a connector connected to the nozzle body that is configured to repeatedly connect and disconnect from the air hose, the connector configured to fluidly connect the inner volume to the air hose when connected to the air hose.

7. An airborne pathogen extraction system comprising:
an extraction nozzle having a nozzle body and a lip, the nozzle body and/or the lip defining a plurality of air extraction openings fluidly connected to the inner volume of the nozzle body; and
an air disinfection unit fluidly connected to the inner volume of the extraction nozzle through an air hose;
wherein the air disinfection unit is configured to generate negative air pressure in the air hose to cause air to flow from an exterior of the extraction nozzle through the plurality of air extraction openings, into the inner volume of the nozzle body, into the air hose, and then to the air disinfection unit; and
wherein the extraction nozzle comprises one or more baffles to eliminate or reduce sounds generated by air moving through the extraction nozzle from reaching an ear of a user of the extraction nozzle.

8. An airborne pathogen extraction system comprising:
an extraction nozzle having a nozzle body and a lip, the nozzle body and/or the lip defining a plurality of air extraction openings fluidly connected to the inner volume of the nozzle body; and
an air disinfection unit fluidly connected to the inner volume of the extraction nozzle through an air hose;
wherein the air disinfection unit is configured to generate negative air pressure in the air hose to cause air to flow from an exterior of the extraction nozzle through the plurality of air extraction openings, into the inner volume of the nozzle body, into the air hose, and then to the air disinfection unit; and
wherein the extraction nozzle has a connector connected to the nozzle body that is configured to repeatedly connect and disconnect from the air hose, the connector configured to fluidly connect the inner volume to the air hose when connected to the air hose.

* * * * *